US007361357B2

(12) United States Patent
Welch et al.

(10) Patent No.: US 7,361,357 B2
(45) Date of Patent: Apr. 22, 2008

(54) SAFE MUTANT VIRAL VACCINES

(75) Inventors: Siao-Kun Wan Welch, Kalamazoo, MI (US); Jay Gregory Calvert, Otsego, MI (US); Michael K. O'Hara, Kalamazoo, MI (US); Xuemei Cao, Scituate, MA (US)

(73) Assignees: Pfizer Inc., New York, NY (US); Pfizer Products Inc., Groton, CT (US)

( * ) Notice: Subject to any disclaimer, the term of this patent is extended or adjusted under 35 U.S.C. 154(b) by 111 days.

(21) Appl. No.: 10/893,712

(22) Filed: Jul. 16, 2004

(65) Prior Publication Data

US 2005/0053621 A1    Mar. 10, 2005

Related U.S. Application Data

(60) Provisional application No. 60/490,834, filed on Jul. 29, 2003.

(51) Int. Cl.
*A61K 39/12* (2006.01)
(52) U.S. Cl. .................................................. 424/218.1
(58) Field of Classification Search ............. 424/204.1, 424/192.1, 218.1; 514/44; 435/320.1, 236
See application file for complete search history.

(56) References Cited

U.S. PATENT DOCUMENTS 6,001,613 A * 12/1999 Donis et al. ................ 435/91.4

2004/0081666 A1* 4/2004 Dominowski ............ 424/202.1

FOREIGN PATENT DOCUMENTS

| WO | WO2004/017990 | 3/2004 |
|---|---|---|
| WO | WO2004/093904 | 11/2004 |

OTHER PUBLICATIONS

Becher et al., "Cytopathogenicity of Border Disease Virus Is Correlated with Integration of Cellular Sequences into the Viral Genome," Journal of Virology, vol. 70, No. 5 (1996).*
Becher et al., "Ribosomal 27a Coding Sequences Upstream of Ubiquitin Coding Sequences in the Genome of a Pestivirus," Journal of Virology, vol. 72, No. 11 (1998), pp. 8697-8704.*
Endsley et al., "Maternal antibody blocks humoral but not T cell responses to BVDV," Biologicals 31, pp. 123-125 (2003).*
Endsley et al., "Bovine Viral Diarrhea Virus Type 1- and Type 2-Sepcific Bovine T lymphocyte-Subset responses Following Modified-Live Virus Vaccination," Veterinary Therapeutics vol. 3, No. 4 (2002), pp. 364-372.*

(Continued)

*Primary Examiner*—Mary E. Mosher
(74) *Attorney, Agent, or Firm*—Timothy J. Gumbleton

(57) ABSTRACT

The present invention provides safe vaccines and methods of preparing such vaccines. The vaccines of the present invention contain at least two live mutant viruses of the same family or nucleic acid molecules encoding such viruses, wherein each of the two viruses or the encoding nucleic acids contains a mutation that confers a desirable phenotype and the mutations in the viruses reside in the same genomic site such that the mutant viruses cannot recombine with each other to eliminate the mutations.

5 Claims, 1 Drawing Sheet

```
                          aa # 1536
NADL                         ↓         90 amino acids
     F  I  R  E  G  N  F  E  G                                P  F  R  Q  E  Y  N  G  F  V  Q  Y
     TTTATAAGGGAAGGCAACTTTGAGGGT  [270 nucleotides]           CCTTTCAGGCAGGAATACAATGGCTTTGTACAATAT
     |||||||||  |||||  |                                      ||| |  || || || || |  || ||||||
     TTTATAAGAGAAGGACGC--------  [393 nucleotides]          -----AGGGAAGAGTATAAGGGTTACGTCCAATAC
     F  I  R  E  G  R                                             R  E  E  Y  K  G  Y  V  Q  Y
53637                           131 amino acids
```

OTHER PUBLICATIONS

Fulton et al., "Antibody responses by cattle after vaccination with commercial viral vaccines containing bovine herpesvirus-1, bovine viral diarrhea virus, parainfluenza-3 virus, and bovine respiratory syncytial virus imunogens and subsequent revaccination at day 140," Vaccine vol. 13, No. 8 (1995) pp. 725-733.*

Mendez et al., "Infectious Bovine Viral Diarrhea Virus (Strain NADL) RNA from Stable cDNA clones: a Cellular Insert Determines NS3 Production and Viral Cytopathogenicity," Journal of Virology, vol. 72, No. 6, (1998), pp. 4737-4745.*

Scherer et al., "Experimental infection of pregnant ewes with bovine viral diarrhea virus type-2 (BVDV-2): effects on the pregnancy and fetus," Veterinary Microbiology 79, pp. 285-299 (2001).*

Willson et al., "Tissue Reaction and Immunity in Swine Immunized with *Actinobacillus pleuropneumoniae* Vaccines," Can. J Vet REs 59: 299-305 (1995).*

Martina Baroth, et. al., "Insertion of Cellular NEDD8 Coding Sequences in Pestivirus", *Virology*, vol. 278, pp. 456-466, (2000).

Paul Becher, et. al., "Nonhomologous RNA Recombination in Bovine Viral Diarrhea Virus: Molecular Characterization of a Variety of Subgenomic RNAs Isolated during an Outbreak of Fatal Mucosal Disease", *Journal of Virology*, vol. 73, No. 7, pp. 5646-5653, (1999).

Paul Becher, et. al., "RNA Recombination between Persisting Pestivirus and a Vaccine Strain: Generation of Cytopathogenic Virus and Induction of Lethal Disease", *Journal of Virology*, vol. 75, No. 14, pp. 6256-6264, (2001).

N. Cammack, et. al., "Intertypic Genomic Rearrangements of Poliovirus Strains in Vaccinees", *Virology*, vol. 167, pp. 507-514, (1988).

Milena Furione, et. al., "Polioviruses with Natural Recombinant Genomes Isolated from Vaccine-Associated Paralytic Poliomyelitis", *Virology*, vol. 196, pp. 199-208, (1993).

Maria-Magdalena Georgescu, et. al., "High Diversity of Poliovirus Strains Isolated from the Central Nervous System from Patients with Vaccine-Associated Paralytic Poliomyelitis", *Journal of Virology*, vol. 68, No. 12, pp. 8089-8101, (1994).

M.-J. Kim, et. al., "Factors regulating template switch in vitro by viral RNA-dependent RNA polymerases: Implications for RNA-RNA recombination", *PNAS*, vol. 98, No. 9, pp. 4972-4977, (2001).

Galina Y. Lipskaya, et. al., "Frequent Isolation of Intertypic Poliovirus Recombinants With Serotype 2 Specificity From Vaccine-Associated Polio Cases", *Journal of Medical Virology*, vol. 35, pp. 290-296, (1991).

Gregor Meyers, et. al., "Molecular Characterization of Pestiviruses", *Advances in Virus Research*, vol. 47, pp. 53-118, (1996).

John D. Neill, et. al., "Recombination with a cellular mRNA encoding a novel DnaJ protein results in biotype conversion in genotype 2 bovine viral diarrhea viruses", *Virus Research*, vol. 79, pp. 59-69, (2001).

J.T. van Oirschot, et. al., "Vaccination of cattle against bovine viral diarrhoea", *Veterinary Microbiology*, vol. 64, pp. 169-183, (1999).

Julia F. Ridpath, et. al., "Delayed Onset Postvaccinal Mucosal Disease as a Result of Genetic Recombination between Genotype 1 and Genotype 2 BVDV", *Virology*, vol. 212, pp. 259-262, (1995).

Julia F. Ridpath, et. al., "Detection and Characterization of Genetic Recombination in Cytopathic Type 2 Bovine Viral Diarrhea Viruses", *Journal of Virology*, vol. 74, No. 18, pp. 8771-8774, (2000).

Štefan Vilček, et. al., "Cellular insertions in the NS2-3 genome region of cytopathic bovine viral diarrhoea virus (BVDV) isolates", *Veterinary Microbiology*, vol. 77, pp. 129-136, (2000).

Li Wang, et. al., "Evolutionary implications of genetic variations in the S1 gene of infectious bronchitis virus", *Virus Research*, vol. 34, pp. 327-338, (1994).

Michael Worobey, et. al., "Evolutionary aspects of recombination in RNA viruses", *Journal of General Virology*, vol. 80, pp. 2535-2543, (1999).

Michael Worobey, et. al., "Widespread intra-serotype recombination in natural populations of dengue virus", *Proc. Natl. Acad. Sci. USA*, vol. 96, pp. 7352-7357, (1999).

Ellsworth, MA, et al., "Efficacy of Bovi-Shield GOLD 5 vaccine against bovine viral diarrhea virus type 2 respiratory challenge," Pfizer Animal Health Technical Bulletin, Nov. 2003, pp. 1-8.

Venugopal, K., et al., "Towards a new generation of flavivirus vaccines," Butterworth Scientific, Guildford, GB, vol. 12, No. 11, Aug. 1994, pp. 966-975.

Widjojoatmodjo, MN, et al., "Classical Swine Fever Virus Erns Deletion Mutants: trans-Complementation and Potential Use as Nontransmissible, Modified, Live-Attenuated Marker Vaccines," Journal of Virology, The American Society of Microbiology, vol. 74, No. 7, Apr. 2000, pp. 2973-2980.

* cited by examiner

SAFE MUTANT VIRAL VACCINES

CROSS REFERENCE TO RELATED APPLICATION

This application claims the benefit of U.S. Provisional Application No. 60/490,834, filed Jul. 29, 2003.

FIELD OF THE INVENTION

The present invention relates generally to vaccines suitable for administration to animals against viral infections. More specifically, the present invention relates to safe vaccines and methods of preparing such vaccines. The vaccines of the present invention contain at least two live mutant viruses of the same family or nucleic add molecules encoding such viruses, wherein each of the viruses or the encoding nucleic adds contains a mutation that confers a desirable phenotype and the mutations in the viruses reside in the same genomic site such that the mutant viruses cannot recombine with each other to eliminate the mutations.

BACKGROUND OF THE INVENTION

The virus family Flaviviridae consists of the genera Pestivirus, Flavivirus and Hepacivirus. The genus Pestivirus is represented by the species Bovine viral diarrhea virus 1 (BVDV-1), BVDV-2, classical swine fever virus, and Border disease virus. The virions of the family members encapsulate positive-strand RNA genomes of about 9.5 to 12.3 kb. The genomic RNAs contain contiguous long open reading frames (ORFs), which are translated into polyproteins that are processed by cellular and viral proteases to give rise to the mature viral proteins. For members of Pestivirus, the ORF encodes a polyprotein of about 3900 amino acids, which is cotranslationally and posttranslationally processed to the following mature viral proteins (from 5' to 3'): $N^{pro}$, C, $E^{ms}$, E1, E2, NS2-3, NS4A, NS4B, NS5A, and NS5B.

Two biotypes are found among some members of Pestivirus based on their effect on tissue culture cells, namely cytopathogenic (cytopathic or cp) and noncytopathogenic (noncytopathic or ncp). Genome analyses revealed insertions of cellular sequences, sometimes accompanied by duplication of viral sequences, genomic rearrangements, and/or deletions of viral sequences in the genomes of cp pestiviruses, but not in the RNAs of the corresponding ncp pestiviruses. This suggests that cp pestiviruses are evolved from ncp pestiviruses by RNA recombination.

BVDV is a widely distributed pathogen of cattle. BVDV-1 usually produces only mild diarrhea in immunocompetent animals, whereas BVDV-2 can produce thrombocytopenia, hemorrhages and acute fatal disease. BVDV is capable of crossing the placenta of pregnant cattle and may result in the birth of persistently infected (PI) calves (Malmquist, J. Am. Vet. Med. Assoc. 152:763-768 (1968); Ross, et al., J. Am. Vet Med. Assoc. 188:618-619 (1986)). Viremic calves are immunotolerant to the virus and persistently viremic for the rest of their lives. They provide a source for outbreaks of mucosal disease (Liess, et al., Dtsch. Tieraerztl. Wschr. 81:481 -487 (1974)) and are highly predisposed to infection with microorganisms causing diseases such as pneumonia or enteric disease (Barber, et al., Vet. Rec. 117:459-464 (1985)). Viruses of either genotype may exist as one of the two biotypes, cp or ncp. The cp phenotype correlates with the expression of NS3, since cells infected with either cp or ncp BVDV both express NS2-3, whereas NS3 is detected only after infection with cp BVDV. NS3 is colinear to the C-terminal part of NS2-3. The expression of NS3 appears to be a result of genomic alterations observed for cp BVDV.

Presently available viral vaccines include killed or attenuated live viral vaccines, live-vectored vaccines, subunit vaccines, and DNA or RNA vaccines. See Roth et al., "New Technology For Improved Vaccine Safety And Efficacy", Veterinary Clinics North America: Food Animal Practice 17(3): 585-597 (2001). Attenuation of viruses can be achieved by UV irradiation, chemical treatment, or high serial passage in vitro. The number, position and nature of mutations induced by these methods are unknown absent genomic sequence analyses. Attenuation can also be achieved by making defined genetic alterations, for example, specific deletion of viral sequences known to confer virulence, or insertion of sequences into the viral genome. One concern with respect to the use of attenuated live viral vaccines is that attenuated mutant viruses have the potential to recombine in vivo to eliminate the attenuating mutation(s) thereby restoring virulence. For example, in the presence of a virulent (wild type) field strain, attenuated viruses having deletions in the viral genome have the potential to recombine with the virulent strain to restore the deleted sequence. See, e.g., Roth et al., supra. Cytopathic pestviruses having cellular insertions have also been observed to give rise to noncytopathic viruses in cell culture by deletion of the cellular sequences, possibly through RNA recombination. See, e.g., Baroth et al., "Insertion of cellular NEDD8 coding sequences in a pestivirus", Virology. 278(2): 456-66, (2000), and Becher et al., "RNA recombination between persisting pestvirus and a vaccine strain: generation of cytopathogenic virus and induction of lethal disease", Journal of Virology 75(14): 6256-64 (2001). Where it is desired to include two attenuated mutant viruses from the same species, genus or family in a vaccine composition, there is a concern that the two viruses may recombine in the vaccinated animal thereby eliminating the attenuating mutations. See, e.g., Glazenburg et al., "Genetic recombination of pseudorabies virus: evidence that homologous recombination between insert sequences is less frequent than between autologous sequences", Archives of Virology, 140(4): 671-85 (1995).

There remains a need to develop safe and effective vaccines that protect animals against viral infections.

SUMMARY OF THE INVENTION

The present invention provides safe vaccines which contain at least two live mutant viruses of the same family or nucleic acid molecules encoding such viruses, wherein each virus or the encoding nucleic acid contains a mutation that confers a desirable phenotype, and the mutations in the viruses reside in the same genomic site such that the mutant viruses cannot recombine with each other to eliminate the mutations.

The present invention also provides a method of preparing a safe viral vaccine by selecting or constructing two or more live mutant viruses of the same family, genus or species, wherein each virus contains a mutation that confers a desirable phenotype, and the mutations in the viruses reside in the same genomic site such that the mutant viruses can not undergo homologous recombination to eliminate the mutations.

The present invention further provides a method of protecting an animal against viral infections by administering to the animal a vaccine composition of the present invention.

DETAILED DESCRIPTION OF THE INVENTION

Figure 1:
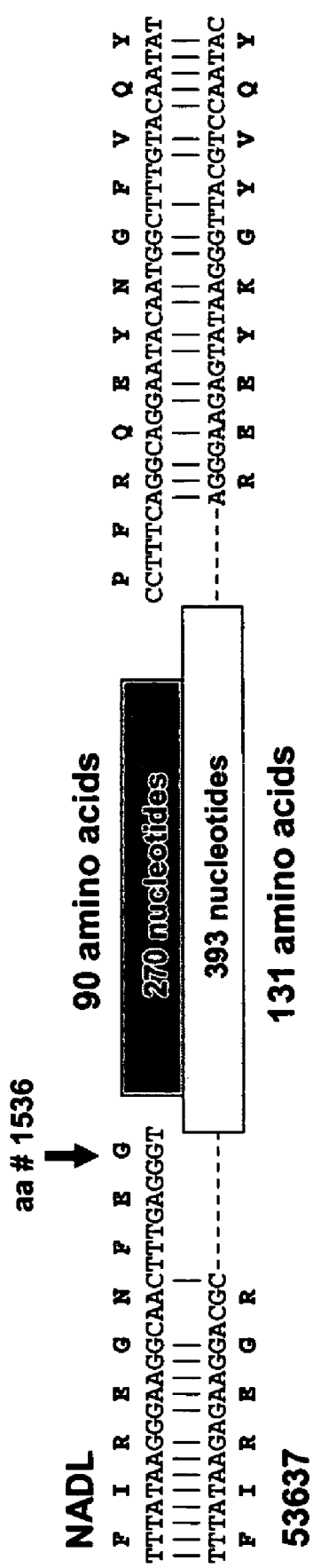
FIG. 1. Alignment of the cellular insertions and flanking viral sequences from the NS2-3 regions of BVDV-1 strain NADL and BVDV-2 strain 53637. The sequences shown in this figure are presented as SEQ ID NOs 11-18 in the sequence listinq.

It has been uniquely recognized in accordance with the present invention that live mutant viruses of the same family, which contain mutations at the same genomic site of the viruses, cannot recombine with one another to eliminate the mutations.

Accordingly, in one embodiment, the present invention provides safe vaccine compositions containing at least two, i.e., two or more, live mutant viruses of the same family, or nucleic acid molecules encoding such viruses, wherein the mutations in the viruses reside in the same genomic site such that the mutant viruses cannot recombine with each other to eliminate the mutations.

In another embodiment, the present invention provides a method of preparing a safe viral vaccine, as described hereinabove. Specifically, a safe vaccine is prepared by selecting or constructing two or more live mutant viruses of the same family, genus or species, wherein each virus contains a mutation that confers a desirable phenotype (for example attenuation of virulence, alteration of cellular tropism or biotype, alteration of species tropism, or expression of a foreign gene cassette), and the mutations in the viruses reside in the same genomic site such that the mutant viruses can not undergo homologous recombination with each other to eliminate the mutations.

The term "vaccine" or "vaccine composition" refers to a composition containing live mutant viruses which, upon inoculation into an animal, induces a complete or partial immunity to the pathogenic version of the viruses, or alleviates the symptoms of diseases caused by the pathogenic versions of the viruses. The protective effects of a vaccine composition against a virus are normally achieved by inducing in the subject an immune response, either a cell-mediated or a humoral immune response, or a combination of both. Generally speaking, abolished or reduced incidences of viral infection, amelioration of the symptoms, or accelerated elimination of the viruses from the infected subjects, are indicative of the protective effects of the vaccine composition.

By "animal" is meant to include birds, for example, chickens, turkeys, domestic waterfowl, and any mammal, for example, cattle, sheep, swine, goats, dogs, cats, and horses.

The term "viruses", "viral isolates" or "viral strains" as used herein refer to viral particles or virions that contain viral genomic DNA or RNA, associated proteins, and other chemical constituents (such as lipids).

By "nucleic acid molecule encoding a virus" or "nucleic acid molecule of a virus" is meant the genomic nucleic acid molecule of the virus, either in the form of RNA or DNA.

By "mutation" is meant to include deletion, insertion or substitution of one or more nucleotides, or a combination thereof. In accordance with the present invention, the mutation preferably confers a desirable phenotype, for example attenuation of virulence, alteration of cellular tropism or biotype, alteration of species tropism, or expression of a foreign gene cassette. Especially preferred mutations are mutations that confer attenuated virulence.

By "attenuation" is meant that the virus has lost some or all of its ability to proliferate and/or cause disease in an animal infected with the virus. For example, an attenuated virus can be a virus that is unable to replicate at all or is limited to one or a few rounds of replication, or restricted in cell or tissue tropism, when present in an animal in which a wild type pathogenic version of the attenuated virus can replicate.

An attenuated virus may have one or more mutations in a gene or genes that are involved in pathogenicity of the virus. Such mutations are also referred to herein as "attenuating mutation(s)". An attenuated virus can be produced from the wild type, pathogenic virus by UV irradiation, chemical treatment, or high serial passage of the wild type, pathogenic virus in vitro. Alternatively, an attenuated virus can be produced from the wild type, pathogenic virus by making specific deletion of viral sequences known to confer virulence, insertion of sequences into the viral genome, or making one or more point mutations in the viral genome. An attenuated virus can be a viral isolate obtained from an animal, which isolate is derived from the wild type, pathogenic version of the virus through events other than artificial means, e.g., events that have occurred in a host animal such as recombination.

The two or more live mutant viruses present in the vaccine compositions of the present invention contain mutations that reside in the same genomic site. By "same genomic site" is meant that when the genomic nucleotide sequences of the viruses are aligned, the mutations in the viral genomes overlap with one another such that there is no opportunity for homologous recombination between and among the viral genomes to eliminate the mutations. In other words, when the genomic nucleotide sequences of the viruses are aligned, there is at least one contiguous portion of the aligned sequences where the sequences in the aligned viral genomes are mutant sequences. There are a number of computer programs that compare and align nucleic acid sequences which one skilled in the art may use. The sequences are aligned for optimal comparison purposes (e.g., gaps can be introduced in a nucleic acid sequence for optimal alignment with a second nucleic acid sequence). For example, the NBLAST and XBLAST programs as described in Altschul, et al., 1990, *J Mol. Biol.* 215:403-410, the Gapped BLAST program as described in Altschul et al., 1997, *Nucleic Acids Res.* 25:3389-3402, and the PSI-Blast program as described in Altschul et al., 1997, *supra*. When utilizing BLAST, Gapped BLAST, and PSI-Blast programs, the default parameters of the respective programs (e.g., XBLAST and NBLAST) can be used (see—the United States government web site from the National Center for Biotechnology Information, US National Library of Medicine, National Institutes of Health).

Generally speaking, the concept of the present invention, i.e., including in the same vaccine composition two or more live mutant viruses of the same family having mutations at the same genomic site, applies to mutant viruses from any family where the viral genomes have sufficient sequence identity to permit homologous recombination. It has been shown that a nucleotide identity as short as 15 nucleotides can lead to efficient homologous recombination (Nagy and Bujarski, *J. Virol.* 69:131-140, 1995).

The present invention applies especially to viruses of the Flaviviridae family. The Flaviviridae family consists of the genera *Pestivirus, Flavivirus* and *Hepacivirus*. The virions of the Flaviviridae family members encapsulate positive-strand RNA genomes of about 9.5 to 12.3 kb. The genomic RNAs containing contiguous long open reading frames, which are translated into polyproteins that are processed by cellular and viral proteases to give rise to the mature viral proteins.

Preferably, the mutant viruses of the vaccine composition of the present invention are from the same genus, either the same or different species.

In a preferred embodiment, the vaccine composition of the present invention contains two or more live mutant viruses from the Pestivirus genus. The genus Pestivirus is represented by the species Bovine Viral Diarrhea Virus Type 1 (BVDV-1), Bovine Viral Diarrhea Virus Type 2 (BVDV-2), classical swine fever virus, and Border disease virus. The ORF encodes a polyprotein of about 3900 amino acids, which is co-translationally and post-translationally processed to the following mature viral proteins (from 5' to 3'): $N^{pro}$, C, $E^{rns}$, E1, E2, NS2-3, NS4A, NS4B, NS5A, and NS5B.

Ordinarily, BVDV has a genome in the form of RNA. RNA can be reverse-transcribed into DNA for use in cloning. Thus, references made herein to nucleic acid and BVD viral sequences encompass both viral RNA sequences and DNA sequences derived from the viral RNA sequences. For convenience, genomic sequences of BVDV as depicted in the SEQUENCE LISTING hereinbelow only refer to the DNA sequences. The corresponding RNA sequence for each is readily apparent to those of skill in the art.

In a more preferred embodiment, the vaccine composition of the present invention contains a cytopathic BVDV-1 and a cytopathic BVDV-2, wherein the mutations in both viruses associated with the cytopathic biotype reside in the same genomic site such that the two mutant viruses cannot recombine to eliminate the mutations.

BVDV-1 and BVDV-2 represent two closely related genotypes of BVDV. The nucleotide sequences of the two viruses share about 70% identity over the entire genome, and slightly higher percent identity within the NS2-3 region. It is believed that the percent identity between the viral genomes of BVDV-1 and BVDV-2, at least in the NS2-3 region, is sufficient to permit homologous recombination.

BVDV-1 usually produce only mild diarrhea in animals, whereas BVDV-2 are viruses with high virulence which can produce thrombocytopenia, hemorrhages and acute fatal disease (Corapi et al., *J. Virol.* 63: 3934-3943; Bolin et al., *Am. J. Vet. Res.* 53: 2157-2163; Pellerin et al., *Virology* 203: 260-268, 1994; Ridpath et al., *Virology* 205: 66-74, 1994; Carman et al., *J. Vet. Diagn. Invest.* 10: 27-35, 1998). The two types of viruses have distinct antigenicity determined by a panel of MAbs and by cross-neutralization using virus-specific antisera raised in animals (Corapi et al., *Am. J. Vet. Res.* 51: 1388-1394, 1990). Viruses of either genotype may exist as one of the two biotypes, cytopathogenic (cytopathic or cp) or noncytopathogenic (noncytopathic or ncp). Cp viruses induce cytopathic effects (e.g., cell lysis) on cultured cells, while noncytopathic viruses do not.

It is desirable to prepare vaccines that provide protection against both BVDV-1 and BVDV-2. However, because of the high degree of sequence identity between the two viruses, there is a possibility that a live cytopathic BVDV-1 and a live cytopathic BVDV-2 included in the same vaccine composition, could recombine with each other in the vaccinated animal to yield noncytopathic viruses. Recombination between BVDV-1 and BVDV-2 has been documented. See, e.g., Ridpath et al., *Virology* 212: 259-262 (1995). Infection of the fetus in pregnant cattle with ncp viruses before immunocompetence develops can result in the fetus remaining viremic through the period of gestation and the subsequent birth of a calf that remains persistently viremic. Such a calf can die of mucosal disease upon superinfecton with a cp BVDV. Accordingly, the vaccine compositions provided by the present invention, which contain live cp BVDV-1 and live cp BVDV-2 having mutations at the same genomic site, are especially desirable for protecting animals against both BVDV-1 and BVDV-2.

In one embodiment, BVDV cp isolates obtained from animals can be used in the vaccine composition of the present invention. Cp isolates of both BVDV-1 and BVDV-2 have been reported and are available to those skilled in the art, e.g., BVDV-1 NADL (ATCC# VR1422 or VR-534), BVDV-2 53637 strain (deposited with the ATCC as PTA4859), and type 2 field isolates such as those described by Ridpath and Neill, *J. Virol.* 74:8771-8774, (2000). Cp isolates reported so far typically contain an insertion of a heterologous sequence, e.g., an ubiquitin coding sequence (Genbank accession number M96687 or De Moerlooze et al., *J. Gen. Virol.* 74:1433-1438, (1993)), a bovine NEDD8 coding sequence (Baroth et al., supra), or a Bos taurus DnaJ1 coding sequence (as described in the Examples hereinbelow), among others.

In another embodiment, a cp BVDV is generated by making defined alterations in the BVDV genome, e.g., by deleting specific viral sequences, inserting sequences into a specific viral genomic site, or making one or more substitutions, or combinations thereof.

Where a cp BVDV is generated by inserting a heterologous (i.e., foreign to the virus) sequence into a specific genomic site, the nature of the sequence to be inserted is generally not critical to the present invention. In addition, the insertion is not limited to any particular site so long as the insertion results in an attenuated phenotype. As heterologous sequences in cp isolates are often found in the NS2-3 region, the NS2-3 region, especially the part surrounding the putative NS2-3 cleavage site which corresponds to, e.g., amino acid residues # 1679 to #1680 of the BVDV-1 NADL strain (the numbering is based on the published genomic sequence Genbank accession No. M31182, SEQ ID NO: 4), is a preferred location for insertions.

An cp BVDV-1 can be generated by making a defined genomic alteration that mimics the mutation identified in a cp BVDV-2 isolate obtained from an animal, such that these viruses have mutations associated with the cp biotype in the same genomic site. Similarly, a cp BVDV-2 can be generated by way of making a defined genomic alteration that mimics the mutation identified in a cp BVDV-1 isolate obtained from an animal.

In a preferred embodiment, the vaccine composition of the present invention contains NADL (a cp BVDV-1 isolate), and BVDV-2 53637 (a cp BVDV-2 isolate), where the two cp isolates each contain a mutation at the same genomic site which results in the cytopathic biotype. The genomic sequence of the BVDV-1 NADL strain is set forth in SEQ ID NO: 4, and the BVDV-2 53637 strain was deposited with the ATCC as PTA-4859. Both isolates contain an insertion in the NS2-3 region. The attenuated cp BVDV-1 contains an insertion of a Bos taurus DnaJ1 coding sequence 3' of the thymidine at nucleotide position # 4993 (NADL sequence numbering), which is the third nucleotide of the codon encoding the glycine residue at amino acid position 1536. The attenuated cp BVDV-2 contains an insertion of a Bos taurus DnaJ1 coding sequence at the same genomic site.

According to the present invention, the cp BVDV isolates employed in the present vaccine composition have been attenuated and are therefore nonpathogenic. Methods of attenuation are known to those skilled in the art and are also described hereinbelow.

In another embodiment, the vaccine composition of the present invention contains an attenuated BVDV-1 and an attenuated BVDV-2, wherein the attenuating mutations in both viruses reside in the same genomic site such that the two mutant viruses cannot recombine to eliminate the attenuating mutations.

An attenuated BVDV is generated by UV irradiation, chemical treatment, or high serial passage of the pathogenic version of the virus in vitro. Sequence analysis can be conducted in order to determine the nature and genomic location of mutations generated by these methods. The mutation can be in the form of a deletion, insertion or substitution of one or more nucleotides, or a combination thereof. Alternatively, an attenuated BVDV is generated by making defined alterations in the BVDV genome, e.g., by deleting specific viral sequences, inserting sequences into a specific viral genomic site, or making one or more substitutions, or combinations thereof.

As described above, the live mutant viruses for use in the vaccine composition of the present invention can be from the same family, genus or species, where the viral genomes have sufficient sequence identity to permit homologous recombination. Additional examples of combinations of viruses appropriate for use in the vaccine composition of the present invention include, but are not limited to, combinations of different types of poliovirus, combinations of multiple live mutant strains of infectious bronchitis virus, combinations of multiple live mutant strains of Newcastle disease virus, combinations of Canine adenovirus-1 and canine adenovirus-2, combinations of equine herpesvirus-1 and equine herpesvirus-4, combinations of multiple live mutant strains of influenza virus, combinations of multiple live attenuated strains of Feline calicivirus, combinations of multiple serotypes of Rotavirus, combinations of multiple serotypes of Rhinovirus, combinations of multiple serotypes of Foot and Mouth Disease virus, combinations of the European and North American genotypes of Porcine reproductive and respiratory syndrome virus, combinations of standard and variant strains of infectious bursal disease virus.

In accordance with the present invention, although viral particles are the preferred form for use in the vaccines, nucleic acid molecules encoding mutant viruses of the same family, genus or species, can be used directly in vaccines as well. The DNA or RNA molecule can be present in a "naked" form or it can be combined with an agent which facilitates cellular uptake (e.g., liposomes or cationic lipids). Vaccines and vaccination procedures that utilize nucleic acids (DNA or mRNA) have been well described in the art, e.g., U.S. Pat. No. 5,703,055, U.S. Pat. No. 5,580,859, U.S. Pat. No. 5,589,466, International Patent Publication WO 98/35562, and by Ramsay et al., 1997, *Immunol. Cell Biol.* 75:360-363; Davis, 1997, *Cur. Opinion Biotech.* 8: 635-640; Manickan et al., 1997, *Critical Rev. Immunol.* 17: 139-154; Robinson, 1997, *Vaccine* 15(8): 785-787; Robinson et al., 1996, *AIDS Res. Hum. Retr.* 12(5): 455-457; Lai and Bennett, 1998, *Critical Rev. Immunol.* 18:449-484; and Vogel and Sarver, 1995, *Clin. Microbiol. Rev.* 8(3): 406-410, all of which are incorporated herein by reference.

In addition to two or more live mutant viruses from the same family, genus or species, the vaccine compositions can include other antigenic component. Other antigenic components appropriate for use in accordance with the present invention include, but are not limited to, antigens prepared from pathogenic bacteria such as *Mycoplasma hyopneumonia, Haemophilus somnus, Haemophilus parasuis, Bordetella bronchiseptica, Bacillus anthracis, Actinobacillus pleuropneumonie, Pasteurella multocida, Mannhemia haemolytica, Mycoplasma bovis, Mycoplasma galanacieum, Mycoplasma gallisepticum, Mycobacterium bovis, Mycobacterium paratuberculosis, Clostridial* spp., *Streptococcus uberis, Streptococcus suis, Staphylococcus aureus, Erysipelothrix rhusopathiae, Campylobacter* spp., *Fusobacterium necrophorum, Escherichia coli, Lawsonia intracellularis, Listeria monocytogenes, Rickettsia rickettsii, Borrelia* spp., *Ehrlichia* spp., *Chlamydia* spp., *Brucella* spp., *Vibrio* spp., *Salmonella enterica serovars, Leptospira* spp.; pathogenic fungi such as *Candida*; protozoa such as *Cryptosporidium parvum, Neospora canium, Toxoplasma gondii, Eimeria* spp., *Babesia* spp., *Giardia* spp.; helminths such as *Ostertagia, Cooperia, Haemonchus, Fasciola*; either in the form of an inactivated whole or partial cell preparation, or in the form of antigenic molecules obtained by genetic engineering techniques or chemical synthesis. Additional antigens include pathogenic viruses such as Marek's disease virus, infectious bursal disease virus, Newcastle's disease virus, chicken anemia virus, fowlpox virus, avian leukosis virus, infectious laryngotracheitis virus, reticuloendothelial virus, canine parvovirus, canine distemper virus, canine herpesvirus, canine coronavirus, canine parainfluenza-5, feline panleukopenia virus, feline herpes virus, feline calicivirus, feline immunodeficiency virus, feline infectious peritonitis virus, equine herpesvirus, equine arteritis virus, equine infectious anemia virus, Eastern equine encephalitis virus, Western equine encephalitis virus, Venezuelan equine encephalitis virus, West Nile virus, transmissible gastroenteritis virus, bovine coronavirus, Bovine herpesviruses-1,3, 6, Bovine parainfluenza virus, Bovine respiratory syncytial virus, bovine leukosis virus, rinderpest virus, foot and mouth disease virus, rabies virus, African swine fever virus, Porcine parvovirus, PRRS virus, Porcine circovirus, influenza virus, swine vesicular disease virus, Techen fever virus, Pseudorabies virus, either in the form of modified live (attenuated) viral preparation, an inactivated whole or partial virus preparation, or in the form of antigenic molecules obtained by genetic engineering techniques or chemical synthesis. When additional attenuated live viruses are used, such additional viruses should preferably be from a family different from that of the two principal attenuated viruses, as described above.

In a preferred embodiment, the present invention provides a vaccine composition which contains an attenuated cp BVDV-1 derived from the BVDV-1 NADL strain, an attenuated cp BVDV-2 derived from the BVDV-2 53637 strain, where the two cp isolates each contain a mutation associated with the cp biotype at the same genomic site, and at least one (i.e., one or more) of the following antigenic component, either in inactivated or modified live form: bovine herpesvirus-1, bovine respiratory syncytial virus, parainfluenza virus-3, *Campylobacter fetus, Leptospira canicola, Leptospira grippotyphosa, Leptospira hardjo, Leptospira icterohaemorrhagiae, Leptospira pomona,* or *Mannhemia haemolytica.*

In addition, the vaccine compositions of the present invention can include one or more veterinarily-acceptable carriers. As used herein, "a veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others. The vaccine compositions can further include one or more other immunomodulatory agents such as, e.g., interleukins, interferons, or other cytokines Adjuvants suitable for use in the vaccine compositions include, but are not limited to, the RIBI adjuvant system (Ribi inc.), alum, aluminum hydroxide gel, oil-in water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, cholesterol, QS-21 (Cambridge Biotech Inc., Cambridge Mass.), or other saponin fractions, monophosphoryl lipid A, Avridine lipid-amine adjuvant, heat-labile enterotoxin from E. coli (recombinant or otherwise), cholera toxin, or muramyl dipeptide, among many others.

Typically, a live mutant virus is present in a vaccine at an amount of about $1 \times 10^6$ and about $1 \times 10^8$ virus particles per dose, with a veterinarily acceptable carrier, in a volume of between about 0.5 and about 5 ml. The precise amount of a virus in a vaccine composition effective to provide a protective effect can be determined by a skilled veterinarian. Where the DNA or RNA molecule of the virus is used in the vaccine, the amount of the nucleic acids should generally be between about 0.1 µg/ml and about 5.0 mg/ml.

The vaccine compositions of the present invention can be made in various forms depending upon the route of administration. For example, the vaccine compositions can be made in the form of sterile aqueous solutions or dispersions suitable for injectable use, or made in lyophilized forms using freeze-drying techniques. Lyophilized compositions are typically maintained at about 4° C., and can be reconstituted in a stabilizing solution, e.g., saline or and HEPES, with or without adjuvant.

The vaccine compositions of the present invention can be administered to an animal for treating or preventing a disease caused by the pathogenic versions of the viruses in the vaccine compositions. Therefore, methods of vaccinating an animal against a disease caused by a virus are also provided by the present invention.

In practicing the present methods, a vaccine composition of the present invention is administered to an animal preferably via parenteral routes, although other routes of administration can be used as well, such as e.g., by oral, intranasal, intramuscular, intra-lymph node, intradermal, intraperitoneal, subcutaneous, rectal or vaginal administration, or by a combination of routes. Boosting regimens may be required and the dosage regimen can be adjusted to provide optimal vaccination.

The present invention is further illustrated by, but by no means limited to, the following examples.

EXAMPLE I

Determination of the Position of the Cellular Insertion in BVDV2 Strain 53637

A portion of the sequence of the NS2-3 region from BVDV2-53637 was determined, in order to identify and map the location of any cellular insertions in the region. A 670 base RT-PCR product was amplified from viral RNA, using forward primer 53637U1 (5'-CGTCCACAGATG-GTTTGGT-3'; SEQ ID NO: 1) and reverse primer 53637L (5'-GGCTATGTATTGGACGTAACCC-3'; SEQ ID NO: 2). The RT-PCR product was purified and submitted for sequence analysis (SEQ ID NO: 3). When aligned with BVDV1-NADL (Genbank accession number M31182, SEQ ID NO: 4), striking similarities were observed (FIG. 1). Both viruses contain an in-frame insertion derived from the Bos taurus DnaJ1 gene. In the case of NADL, the insertion is 90 amino acids (270 nucleotides) in length and is located between glycine-1536 and proline-1627 in the NADL polyprotein. These coordinates correspond to glycine-1536 and proline-1537 in non-cytopathic BVDV1 strains such as SD-1 (Genbank accession number AAA42860, SEQ ID NO: 6), indicating that the genome alteration in NADL is a simple insertion with no concomitant deletion or duplication of flanking viral sequences. Like BVDV1-NADL, there is an insertion of a portion of the Bos taurus DnaJ1 gene in BVDV2-53637. The cellular insertion is longer (131 amino acids, 393 nucleotides), being extended in both directions relative to the insertion in BVDV1-NADL. The location of the cellular insertion within the NS2-3 region is identical in the two viruses. Unlike BVDV1-NADL, the BVDV2-53637 insertion is accompanied by a deletion of 5 amino acids (15 nucleotides) of flanking viral sequences. Three amino acid residues are absent flanking the 5' end of the insertion, while two amino acids residues are absent flanking the 3' end of the insertion. Because the cellular insertions are at the same genome position in the two vaccine viruses, they cannot undergo homologous recombination to delete the insertion to generate a non-cytopathic chimeric virus.

EXAMPLE II

Attempts to Detect Non-Cytopathic BVDV Viruses in Co-passaged BVDV1-NADL/BVDV2-53637 Cultures In order to determine whether the two vaccine viruses are capable of recombining to generate detectable levels of non-cytopathic BVDV, the viruses were co-cultivated on susceptible cells and a sensitive hemi-nested RT-PCR assay was used to detect potential non-cytopathic viruses from among an excess of longer cytopathic products that still contain the cellular insert. To increase the probability of intertypic recombination in vitro, each virus was inoculated simultaneously onto confluent BK-6 cells in 6-well plates at a multiplicity of infection of 2-4 (12 replicates per experiment). After 2-3 days of co-cultivabon the cells were frozen and thawed twice, and cell debris was removed by low speed centrifugation. The resulting supernatant fluid was then used as inoculum for the next passage. A total of seven serial passages were conducted in several studies. During the passages BVDV1-NADL grew more rapidly than BVDV2-53637, but the type II virus was still detectable after seven passages using nested RT-PCR. A sensitive hemi-nested RT-PCR assay was employed in an attempt to detect any non-cytopathic virus.

In first round RT-PCR, forward primers 53637U1 (SEQ ID NO: 1) or NADL4744 (5'-CGTGGCTTCTTGG-TACGGG-3',SEQ ID NO: 7) were used in conjuncton with reverse primers 53637L (SEQ ID NO: 2) or NADL5305 (5'-AGCGGTATATTGTACAAAGCCA-3', SEQ IDNO: 8). All four combinations of forward and reverse primers were used in order to detect BVDV1, BVDV2, and intertypic recombinants. The expected size of RT-PCR product was 562 bp for cytopathic BVDV1-NADL and 670 bp for cytopathic BVDV2-53637. Non-cytopathic viruses, if present at detectible levels, would be expected to yield first round products of 292 bp (BVDV1-NADL) or 277 bp (BVDV2-53637). Intertypic recombinants should be similar in size to one of the parents, or of intermediate length, depending on the location of the recombination site. Non-cytopathic BVDVs were never detected following first round RT-PCR.

To increase the sensitivity of detecting non-cytopathic BVDV in the presence of a large excess of cytopathic BVDV, a restriction enzyme digestion step was included before the nested PCR to destroy the larger NS2-3 templates derived from the cytopathic viruses. A combination of Mspl and Dral was selected based on the observation that they cut within the Bos taurus DnaJ1 insert but do not cut the flanking viral sequences. In second round (hemi-nested) PCR, forward primers 53637U2 (5'-TGCACGATCTGT-GAAGGGAAAGAA-3', SEQ ID NO: 9) or NADL4844 (5'-TGCACTGTATGTGAGGGCCGAGAG-3', SEQ ID NO: 10) were used in conjunction with the same two reverse primers 53637L or NADL5305. Appropriate primer combinations were used to attempt to detect intertypic recombinants as well as BVDV1 and BVDV2. The expected size of RT-PCR product is 462 bp for cytopathic BVDV1-NADL and 570 bp for cytopathic BVDV2-53637 (present at low levels due to incomplete digestion of the cytopathic BVDV RT-PCR products). Non-cytopathic viruses, if present at detectable levels, would be expected to yield second round products of 192 bp (BVDV1-NADL) or 177 bp (BVDV2-53637). Intertypic recombinants should be similar in size to one of the parents, or of intermediate length, depending on the location of the recombination site. Non-cytopathic BVDVs were never detected following second round PCR. In a few individual reactions, aberrant bands of various sizes were seen. All bands between 100 and 300 bp were considered to be potential non-cytopathic products and were submitted for DNA sequence analysis. In every case the aberrant band was the result of false priming during PCR. There was no evidence of non-cytopathic virus in any of the studies.

| SEQ ID NO | DESCRIPTION |
|---|---|
| 1 | forward primer 53637U1 |
| 2 | reverse primer 53637L |
| 3 | 670 bp RT-PCR product from the NS2-3 region of BVDV2 strain 53637 |
| 4 | genomic sequence of BVDV1-NADL (Genbank accession number M31182) |
| 5 | polyprotein sequence of BVDV1-NADL (Genbank accession number AAA42854) |
| 6 | polyprotein sequence of non-cytopathic BVDV1 strain SD-1 (Genbank accession number AAA42860) |
| 7 | forward primer NADL4744 |
| 8 | reverse primer NADL5305 |
| 9 | forward primer 53637U2 |
| 10 | forward primer NADL4844 |

SEQ NO: 1
cgtccacagatggtttggt

SEQ NO: 2
ggctatgtattggacgtaaccc

SEQ NO: 3
cgtccacagatggtttggtgaggaggaaatatatggggcacccaaggtgatcaccatcataaaagctagtac cctaagtaaaaacaggcactgcataatctgcacgatctgtgaagggaaagaatggaacggagccaactgccc aaagtgtggaagacaaggaaagcccataacatgtggaatgacactcgcagactttgaggagaaacattacaa aaagatatttataagagaaggacgccaagaagcaatgaatacgatgatgtgcagccgatgccagggaaagca taggaggtttgaaacggaccgggaacctaagagtgccagatactgtgctgagtgtaataggctgcatcctgc tgaggaaggtgacttttgggcagagtcaagcatgttgggcctcaaaatcacctactttgcgctgatggatgg aaaggtgtatgatatcacagagtgggctggatgccagcgtgtgggaatctccccagatacccacagagtccc ttgtcacatctcatttggttcacggatgccaggcaccagtgggcggcagagagctactccagatgcccctcc tgctgaccttcaggatttcttgagccggatctttcaagtacccccaggccagatgtccagggaagagtataa gggttacgtccaatacatagcc SEQ ID: 4
gtatacgaga attagaaaag gcactcgtat acgtattggg caattaaaaa taataattag gcctagggaa caaatccctc tcagcgaagg ccgaaaagag gctagccatg cccttagtag gactagcata atgagggggg tagcaacagt ggtgagttcg ttggatggct taagccctga gtacagggta gtcgtcagtg gttcgacgcc ttggaataaa ggtctcgaga tgccacgtgg acgagggcat gcccaaagca catcttaacc tgagcggggg tcgcccaggt aaaagcagtt ttaaccgact gttacgaata cagcctgata gggtgctgca gaggcccact gtattgctac taaaaatctc tgctgtacat ggcacatgga gttgatcaca aatgaacttt tatacaaaac -continued

```
atacaaacaa aaacccgtcg gggtggagga acctgtttat gatcaggcag gtgatccctt atttggtgaa aggggagcag tccaccctca atcgacgcta aagctcccac acaagagagg ggaacgcgat gttccaacca acttggcatc cttaccaaaa agaggtgact gcaggtcggg taatagcaga ggacctgtga gcgggatcta cctgaagcca gggccactat tttaccagga ctataaaggt cccgtctatc acagggcccc gctggagctc tttgaggagg gatccatgtg tgaaacgact aaacggatag ggagagtaac tggaagtgac ggaaagctgt accacattta tgtgtgtata gatggatgta taataataaa aagtgccacg agaagttacc aaagggtgtt caggtgggtc cataataggc ttgactgccc tctatgggtc acaacttgct cagacacgaa agaagaggga gcaacaaaaa agaaaacaca gaaacccgac agactagaaa gggggaaaat gaaatagtg cccaaagaat ctgaaaaaga cagcaaaact aaacctccgg atgctacaat agtggtggaa ggagtcaaat accaggtgag gaagaaggga aaaccaaga gtaaaaacac tcaggacggc ttgtaccata acaaaaacaa acctcaggaa tcacgcaaga aactggaaaa agcattgttg gcgtgggcaa taatagctat agttttgttt caagttacaa tgggagaaaa cataacacag tggaacctac aagataatgg gacggaaggg atacaacggg caatgttcca aaggggtgtg aatagaagtt tacatggaat ctggccagag aaaatctgta ctggcgtccc ttcccatcta gccaccgata tagaactaaa aacaattcat ggtatgatgg atgcaagtga gaagaccaac tacacgtgtt gcagacttca acgccatgag tggaacaagc atggttggtg caactggtac aatattgaac cctggattct agtcatgaat agaacccaag ccaatctcac tgagggacaa ccaccaaggg agtgcgcagt cacttgtagg tatgataggg ctagtgactt aaacgtggta acacaagcta gagatagccc cacacccta acaggttgca agaaaggaaa gaacttctcc tttgcaggca tattgatgcg gggcccctgc aactttgaaa tagctgcaag tgatgtatta ttcaaagaac atgaacgcat tagtatgttc caggatacca ctctttacct tgttgacggg ttgaccaact ccttagaagg tgccagacaa ggaaccgcta aactgacaac ctggttaggc aagcagctcg ggatactagg aaaaagttg gaaaacaaga gtaagacgtg gtttggagca tacgctgctt ccccttactg tgatgtcgat cgcaaaattg gctacatatg gtatacaaaa aattgcaccc ctgcctgctt acccaagaac acaaaaattg tcggccctgg gaaatttggc accaatgcag aggacggcaa gatattacat gagatggggg gtcacttgtc ggaggtacta ctactttctt tagtggtgct gtccgacttc gcaccggaaa cagctagtgt aatgtaccta atcctacatt tttccatccc acaaagtcac gttgatgtaa tggattgtga taagacccag ttgaacctca cagtggagct gacaacagct gaagtaatac cagggtcggt ctggaatcta ggcaaatatg tatgtataag accaaattgg tggccttatg agacaactgt agtgttggca tttgaagagg tgagccaggt ggtgaagtta gtgttgaggg cactcagaga tttaacacgc atttggaacg ctgcaacaac tactgctttt ttagtatgcc ttgttaagat agtcaggggc cagatggtac agggcattct gtggctacta ttgataacag ggtacaagg gcacttggat tgcaaacctg aattctcgta tgccatagca aaggacgaaa gaattggtca actgggggct gaaggcctta ccaccacttg gaaggaatac tcacctggaa tgaagctgga agacacaatg gtcattgctt ggtgcgaaga tgggaagtta atgtacctcc aaagatgcac gagagaaacc agatatctcg caatcttgca tacaagagcc ttgccgacca gtgtggtatt caaaaaactc tttgatgggc gaaagcaaga ggatgtagtc gaaatgaacg acaactttga atttggactc tgcccatgtg atgccaaacc catagtaaga gggaagttca atacaacgct
```

```
gctgaacgga ccggccttcc agatggtatg ccccatagga tggacaggga ctgtaagctg
tacgtcattc aatatggaca ccttagccac aactgtggta cggacatata aaggtctaa
accattccct cataggcaag gctgtatcac ccaaaagaat ctgggggagg atctccataa
ctgcatcctt ggaggaaatt ggacttgtgt gcctggagac caactactat acaaaggggg
ctctattgaa tcttgcaagt ggtgtggcta tcaatttaaa gagagtgagg gactaccaca
ctaccccatt ggcaagtgta aattggagaa cgagactggt tacaggctag tagacagtac
ctcttgcaat agagaaggtg tggccatagt accacaaggg acattaaagt gcaagatagg
aaaaacaact gtacaggtca tagctatgga taccaaactc ggacctatgc cttgcagacc
atatgaaatc atatcaagtg aggggcctgt agaaaagaca gcgtgtactt tcaactacac
taagacatta aaaaataagt attttgagcc cagagacagc tactttcagc aatacatgct
aaaaggagag tatcaatact ggtttgacct ggaggtgact gaccatcacc gggattactt
cgctgagtcc atattagtgg tggtagtagc cctcttgggt ggcagatatg tactttggtt
actggttaca tacatggtct tatcagaaca gaaggcctta gggattcagt atggatcagg
ggaagtggtg atgatgggca acttgctaac ccataacaat attgaagtgg tgacatactt
cttgctgctg tacctactgc tgagggagga gagcgtaaag aagtgggtct tactcttata
ccacatctta gtggtacacc caatcaaatc tgtaattgtg atcctactga tgattgggga
tgtggtaaag gccgattcag ggggccaaga gtacttgggg aaaatagacc tctgttttac
aacagtagta ctaatcgtca taggtttaat catagctagg cgtgacccaa ctatagtgcc
actggtaaca ataatggcag cactgagggt cactgaactg acccaccagc ctggagttga
catcgctgtg gcggtcatga ctataaccct actgatggtt agctatgtga cagattattt
tagatataaa aaatggttac agtgcattct cagcctggta tctgcggtgt tcttgataag
aagcctaata tacctaggta gaatcgagat gccagaggta actatcccaa actggagacc
actaactta atactattat atttgatctc aacaacaatt gtaacgaggt ggaaggttga
cgtggctggc ctattgttgc aatgtgtgcc tatcttattg ctggtcacaa ccttgtgggc
cgacttctta accctaatac tgatcctgcc tacctatgaa ttggttaaat tatactatct
gaaaactgtt aggactgata cagaaagaag ttggctaggg gggatagact atacaagagt
tgactccatc tacgacgttg atgagagtgg agagggcgta tatctttttc catcaaggca
gaaagcacag gggaatttt ctatactctt gcccttatc aaagcaacac tgataagttg
cgtcagcagt aaatggcagc taatatacat gagttactta actttggact ttatgtacta
catgcacagg aaagttatag aagagatctc aggaggtacc aacataatat ccaggttagt
ggcagcactc atagagctga actggtccat ggaagaagag gagagcaaag gcttaaagaa
gttttatcta ttgtctggaa ggttgagaaa cctaataata aaacataagg taaggaatga
gaccgtggct tcttggtacg gggaggagga agtctacggt atgccaaaga tcatgactat
aatcaaggcc agtacactga gtaagagcag gcactgcata atatgcactg tatgtgaggg
ccgagagtgg aaaggtggca cctgcccaaa atgtggacgc catgggaagc cgataacgtg
tgggatgtcg ctagcagatt ttgaagaaag acactataaa agaatcttta agggaagg
caactttgag ggtatgtgca gccgatgcca gggaaagcat aggaggtttg aaatggaccg
ggaacctaag agtgccagat actgtgctga gtgtaatagg ctgcatcctg ctgaggaagg
tgacttttgg gcagagtcga gcatgttggg cctcaaaatc acctactttg cgctgatgga
tggaaaggtg tatgatatca cagagtgggc tggatgccag cgtgtgggaa tctccccaga
```

-continued

```
tacccacaga gtcccttgtc acatctcatt tggttcacgg atgcctttca ggcaggaata
caatggcttt gtacaatata ccgctagggg gcaactattt ctgagaaact tgcccgtact
ggcaactaaa gtaaaaatgc tcatggtagg caaccttgga gaagaaattg gtaatctgga
acatcttggg tggatcctaa gggggcctgc cgtgtgtaag aagatcacag agcacgaaaa
atgccacatt aatatactgg ataaactaac cgcattttc gggatcatgc caaggggac
tacacccaga gccccggtga ggttccctac gagcttacta aaagtgagga ggggtctgga
gactgcctgg gcttacacac accaaggcgg gataagttca gtcgaccatg taaccgccgg
aaaagatcta ctggtctgtg acagcatggg acgaactaga gtggtttgcc aaagcaacaa
caggttgacc gatgagacag agtatggcgt caagactgac tcagggtgcc cagacggtgc
cagatgttat gtgttaaatc cagaggccgt taacatatca ggatccaaag gggcagtcgt
tcacctccaa aagacaggtg gagaattcac gtgtgtcacc gcatcaggca caccggcttt
cttcgaccta aaaaacttga aaggatggtc aggcttgcct atatttgaag cctccagcgg
gagggtggtt ggcagagtca agtagggaa gaatgaagag tctaaaccta caaaaataat
gagtggaatc cagaccgtct caaaaaacag agcagacctg accgagatgg tcaagaagat
aaccagcatg aacaggggag acttcaagca gattactttg gcaacagggg caggcaaaac
cacagaactc ccaaaagcag ttatagagga gataggaaga cacaagagag tattagttct
tataccatta agggcagcgg cagagtcagt ctaccagtat atgagattga acacccaag
catctctttt aacctaagga tagggacat gaaagagggg gacatggcaa ccgggataac
ctatgcatca tacgggtact tctgccaaat gcctcaacca aagctcagag ctgctatggt
agaatactca tacatattct tagatgaata ccattgtgcc actcctgaac aactggcaat
tatcgggaag atccacagat tttcagagag tataagggtt gtcgccatga ctgccacgcc
agcagggtcg gtgaccacaa caggtcaaaa gcacccaata gaggaattca tagcccccga
ggtaatgaaa ggggaggatc ttggtagtca gttccttgat atagcagggt taaaaatacc
agtggatgag atgaaaggca atatgttggt ttttgtacca acgagaaaca tggcagtaga
ggtagcaaag aagctaaaag ctaagggcta taactctgga tactattaca gtggagagga
tccagccaat ctgagagttg tgacatcaca atcccctat gtaatcgtgg ctacaaatgc
tattgaatca ggagtgacac taccagattt ggacacggtt atagacacgg ggttgaaatg
tgaaagagg gtgagggtat catcaaagat acccttcatc gtaacaggcc ttaagaggat
ggccgtgact gtgggtgagc aggcgcagcg taggggcaga gtaggtagag tgaaacccgg
gaggtattat aggagccagg aaacagcaac agggtcaaag gactaccact atgacctctt
gcaggcacaa agatacggga ttgaggatgg aatcaacgtg acgaaatcct ttagggagat
gaattacgat tggagcctat acgaggagga cagcctacta ataacccagc tggaaatact
aaataatcta ctcatctcag aagacttgcc agccgctgtt aagaacataa tggccaggac
tgatcaccca gagccaatcc aacttgcata caacagctat gaagtccagg tcccggtcct
attcccaaaa ataaggaatg gagaagtcac agacacctac gaaaattact cgtttctaaa
tgccagaaag ttaggggagg atgtgcccgt gtatatctac gctactgaag atgaggatct
ggcagttgac ctcttagggc tagactggcc tgatcctggg aaccagcagg tagtggagac
tggtaaagca ctgaagcaag tgaccgggtt gtcctcggct gaaaatgccc tactagtggc
tttatttggg tatgtgggtt accaggctct ctcaaagagg catgtcccaa tgataacaga
catatatacc atcgaggacc agagactaga agacaccacc cacctccagt atgcacccaa
```

-continued

```
cgccataaaa accgatggga cagagactga actgaaagaa ctggcgtcgg gtgacgtgga aaaaatcatg ggagccattt cagattatgc agctggggga ctggagtttg ttaaatccca agcagaaaag ataaaaacag ctcctttgtt taaagaaaac gcagaagccg caaaagggta tgtccaaaaa ttcattgact cattaattga aaataaagaa gaaataatca gatatggttt gtggggaaca cacacagcac tatacaaaag catagctgca agactggggc atgaaacagc gtttgccaca ctagtgttaa agtggctagc ttttggaggg gaatcagtgt cagaccacgt caagcaggcg gcagttgatt tagtggtcta ttatgtgatg aataagcctt ccttcccagg tgactccgag acacagcaag aagggaggcg attcgtcgca agcctgttca tctccgcact ggcaacctac acatacaaaa cttggaatta ccacaatctc tctaaagtgg tggaaccagc cctggcttac ctcccctatg ctaccagcgc attaaaaatg ttcacccccaa cgcggctgga gagcgtggtg atactgagca ccacgatata taaaacatac ctctctataa ggaaggggaa gagtgatgga ttgctgggta cggggataag tgcagccatg gaaatcctgt cacaaaaccc agtatcggta ggtatatctg tgatgttggg ggtaggggca atcgctgcgc acaacgctat tgagtccagt gaacagaaaa ggaccctact tatgaaggtg tttgtaaaga acttcttgga tcaggctgca acagatgagc tggtaaaaga aaacccagaa aaaattataa tggccttatt tgaagcagtc cagacaattg gtaaccccct gagactaata taccacctgt atggggttta ctacaaaggt tgggaggcca aggaactatc tgagaggaca gcaggcagaa acttattcac attgataatg tttgaagcct tcgagttatt agggatggac tcacaaggga aaataaggaa cctgtccgga aattacattt tggatttgat atacggccta cacaagcaaa tcaacagagg gctgaagaaa atggtactgg ggtgggcccc tgcacccttt agttgtgact ggaccccctag tgacgagagg atcagattgc caacagacaa ctatttgagg gtagaaacca ggtgcccatg tggctatgag atgaaagctt tcaaaaatgt aggtggcaaa cttaccaaag tggaggagag cgggcctttc ctatgtagaa acagacctgg tagggaccca gtcaactaca gagtcaccaa gtattacgat gacaacctca gagagataaa accagtagca aagttggaag gacaggtaga gcactactac aaaggggtca cagcaaaaat tgactacagt aaaggaaaaa tgctcttggc cactgacaag tgggaggtgg aacatggtgt cataaccagg ttagctaaga gatatactgg ggtcgggttc aatggtgcat acttaggtga cgagcccaat caccgtgctc tagtggagag ggactgtgca actataacca aaaacacagt acagtttcta aaaatgaaga aggggtgtgc gttcacctat gacctgacca tctccaatct gaccaggctc atcgaactag tacacaggaa caatcttgaa gagaaggaaa tacccaccgc tacggtcacc acatggctag cttacacctt cgtgaatgaa gacgtaggga ctataaaacc agtactagga gagagagtaa tccccgaccc tgtagttgat atcaatttac aaccagaggt gcaagtggac acgtcagagg ttgggatcac aataattgga agggaaaccc tgatgacaac gggagtgaca cctgtcttgg aaaaagtaga gcctgacgcc agcgacaacc aaaactcggt gaagatcggg ttggatgagg gtaattaccc agggcctgga atacagacac atacactaac agaagaaata cacaacaggg atgcgaggcc cttcatcatg atcctgggct caaggaattc catatcaaat agggcaaaga ctgctagaaa tataaatctg tacacaggaa atgaccccag ggaaatacga gacttgatgg ctgcagggcg catgttagta gtagcactga gggatgtcga ccctgagctg tctgaaatgg tcgatttcaa ggggacttttt ttagataggg aggccctgga ggctctaagt ctcgggcaac ctaaaccgaa gcaggttacc aaggaagctg ttaggaattt gatagaacag aaaaaagatg tggagatccc
```

-continued

```
taactggttt gcatcagatg acccagtatt tctggaagtg gccttaaaaa atgataagta
ctacttagta ggagatgttg gagagctaaa agatcaagct aaagcacttg gggccacgga
tcagacaaga attataaagg aggtaggctc aaggacgtat gccatgaagc tatctagctg
gttcctcaag gcatcaaaca aacagatgag tttaactcca ctgtttgagg aattgttgct
acggtgccca cctgcaacta agagcaataa ggggcacatg gcatcagctt accaattggc
acagggtaac tgggagcccc tcggttgcgg ggtgcaccta ggtacaatac cagccagaag
ggtgaagata cacccatatg aagcttacct gaagttgaaa gatttcatag aagaagaaga
gaagaaacct agggttaagg atacagtaat aagagagcac aacaaatgga tacttaaaaa
ataaggttt caaggaaacc tcaacaccaa gaaaatgctc aacccaggga aactatctga
acagttggac agggaggggc gcaagaggaa catctacaac caccagattg gtactataat
gtcaagtgca ggcataaggc tggagaaatt gccaatagtg agggcccaaa ccgacaccaa
aacctttcat gaggcaataa gagataagat agacaagagt gaaaaccggc aaaatccaga
attgcacaac aaattgttgg agattttcca cacgatagcc caacccaccc tgaaacacac
ctacggtgag gtgacgtggg agcaacttga ggcgggggta aatagaaagg gggcagcagg
cttcctggag aagaagaaca tcggagaagt attggattca gaaaagcacc tggtagaaca
attggtcagg gatctgaagg ccgggagaaa gataaaatat tatgaaactg caataccaaa
aaatgagaag agagatgtca gtgatgactg gcaggcaggg gacctggtgg ttgagaagag
gccaagagtt atccaatacc ctgaagccaa gacaaggcta gccatcacta aggtcatgta
taactgggtg aaacagcagc ccgttgtgat tccaggatat gaaggaaaga ccccccttgtt
caacatcttt gataaagtga gaaaggaatg ggactcgttc aatgagccag tggccgtaag
ttttgacacc aaagcctggg acactcaagt gactagtaag gatctgcaac ttattggaga
aatccagaaa tattactata agaaggagtg gcacaagttc attgacacca tcaccgacca
catgacagaa gtaccagtta aacagcaga tggtgaagta tatataagaa atgggcagag
agggagcggc cagccagaca caagtgctgg caacagcatg ttaaatgtcc tgacaatgat
gtacggcttc tgcgaaagca caggggtacc gtacaagagt ttcaacaggg tggcaaggat
ccacgtctgt ggggatgatg gcttcttaat aactgaaaaa gggttagggc tgaaatttgc
taacaaaggg atgcagattc ttcatgaagc aggcaaacct cagaagataa cggaagggga
aaagatgaaa gttgcctata gatttgagga tatagagttc tgttctcata ccccagtccc
tgttaggtgg tccgacaaca ccagtagtca catggccggg agagacaccg ctgtgatact
atcaaagatg gcaacaagat tggattcaag tggagagagg ggtaccacag catatgaaaa
agcggtagcc ttcagtttct tgctgatgta ttcctggaac ccgcttgtta ggaggatttg
cctgttggtc ctttcgcaac agccagagac agacccatca aaacatgcca cttattatta
caaaggtgat ccaataggg cctataaaga tgtaataggt cggaatctaa gtgaactgaa
gagaacaggc tttgagaaat tggcaaatct aaacctaagc ctgtccacgt tggggggtctg
gactaagcac acaagcaaaa gaataattca ggactgtgtt gccattggga agaagaggg
caactggcta gttaagcccg acaggctgat atccagcaaa actggccact tatacatacc
tgataaaggc tttacattac aaggaaagca ttatgagcaa ctgcagctaa gaacagagac
aaacccggtc atgggggttg ggactgagag atacaagtta ggtcccatag tcaatctgct
gctgagaagg ttgaaaattc tgctcatgac ggccgtcggc gtcagcagct gagacaaaat
gtatatattg taaataaatt aatccatgta catagtgtat ataaatatag ttgggaccgt
```

-continued

```
ccacctcaag aagacgacac gcccaacacg cacagctaaa cagtagtcaa gattatctac
ctcaagataa cactacattt aatgcacaca gcactttagc tgtatgagga tacgcccgac
gtctatagtt ggactaggga agacctctaa cag
SEQ ID: 5
melitnelly ktykqkpvgv eepvydqagd plfgergavh pqstlklphk rgerdvptnl
aslpkrgdcr sgnsrgpvsg iylkpgplfy qdykgpvyhr aplelfeegs mcettkrigr
vtgsdgklyh iyvcidgcii iksatrsyqr vfrwvhnrld cplwvttcsd tkeegatkkk
tqkpdrlerg kmkivpkese kdsktkppda tivvegvkyq vrkkgktksk ntqdglyhnk
nkpqesrkkl ekallawaii aivlfqvtmg enitqwnlqd ngtegiqram fqrgvnrslh
giwpekictg vpshlatdie lktihgmmda sektnytccr lqrhewnkhg wcnwyniepw
ilvmnrtqan ltegqpprec avtcrydras dlnvvtqard sptpltgckk gknfsfagil
mrgpcnfeia asdvlfkehe rismfqdttl ylvdgltnsl egarqgtakl ttwlgkqlgi
lgkklenksk twfgayaasp ycdvdrkigy iwytknctpa clpkntkivg pgkfgtnaed
gkilhemggh lsevlllslv vlsdfapeta svmylilhfs ipqshvdvmd cdktqlnltv
elttaevipg svwnlgkyvc irpnwwpyet tvvlafeevs qvvklvlral rdltriwnaa
tttaflvclv kivrgqmvqg ilwlllitgv qghldckpef syaiakderi gqlgaegltt
twkeyspgmk ledtmviawc edgklmylqr ctretrylai lhtralptsv vfkklfdgrk
qedvvemndn fefglcpcda kpivrgkfnt tllngpafqm vcpigwtgtv sctsfnmdtl
attvvrtyrr skpfphrqgc itqknlgedl hncilggnwt cvpgdqllyk ggiesckwc
gyqfkesegl phypigkckl enetgyrlvd stscnregva ivpqgtlkck igkttvqvia
mdtklgpmpc rpyeiisseg pvektactfn ytktlknkyf eprdsyfqqy mlkgeyqywf
dlevtdhhrd yfaesilvvv vallggryvl wllvtymvls eqkalgiqyg sgevvmmgnl
lthnnievvt yflllylllr eesvkkwvll lyhilvvhpi ksvivillmi gdvvkadsgg
qeylgkidlc fttvvlivig liiarrdpti vplvtimaal rvtelthqpg vdiavavmti
tllmvsyvtd yfrykkwlqc ilslvsavfl irsliylgri empevtipnw rpltlillyl
isttivtrwk vdvaglllqc vpilllvttl wadfltlili lptyelvkly ylktvrtdte
rswlggidyt rvdsiydvde sgegvylfps rqkaqgnfsi llplikatli scvsskwqli
ymsyltldfm yymhrkviee isggtniisr lvaalielnw smeeeeskgl kkfyllsgrl
rnliikhkvr netvaswyge eevygmpkim tiikastlsk srhciictvc egrewkggtc
pkcgrhgkpi tcgmsladfe erhykrifir egnfegmcsr cqgkhrrfem drepksaryc
aecnrlhpae egdfwaessm lglkityfal mdgkvydite wagcqrvgis pdthrvpchi
sfgsrmpfrq eyngfvqyta rgqlflrnlp vlatkvkmlm vgnlgeeign lehlgwilrg
pavckkiteh ekchinildk ltaffgimpr gttprapvrf ptsllkvrrg letawaythq
ggissvdhvt agkdllvcds mgrtrvvcqs nnrltdetey gvktdsgcpd garcyvlnpe
avnisgskga vvhlqktgge ftcvtasgtp affdlknlkg wsglpifeas sgrvvgrvkv
gkneeskptk imsgiqtvsk nradltemvk kitsmnrgdf kqitlatgag kttelpkavi
eeigrhkrvl vliplraaae svyqymrlkh psisfnlrig dmkegdmatg ityasygyfc
qmpqpklraa mveysyifld eyhcatpeql aiigkihrfs esirvvamta tpagsvtttg
qkhpieefia pevmkgedlg sqfldiaglk ipvdemkgnm lvfvptrnma vevakklkak
gynsgyyysg edpanlrvvt sqspyvivat naiesgvtlp dldtvidtgl kcekrvrvss
```

-continued kipfivtglk rmavtvgeqa qrrgrvgrvk pgryyrsqet atgskdyhyd llqaqrygie dginvtksfr emnydwslye edsllitqle ilnnllised lpaavknima rtdhpepiql aynsyevqvp vlfpkirnge vtdtyenysf lnarklgedv pvyiyatede dlavdllgld wpdpgnqqvv etgkalkqvt glssaenall valfgyvgyq alskrhvpmi tdiytiedqr ledtthlqya pnaiktdgte telkelasgd vekimgaisd yaagglefvk sqaekiktap lfkenaeaak gyvqkfidsl ienkeeiiry glwgthtaly ksiaarlghe tafatlvlkw lafggesvsd hvkqaavdlv vyyvmnkpsf pgdsetqqeg rrfvaslfis alatytyktw nyhnlskvve palaylpyat salkmftptr lesvvilstt iyktylsirk gksdgllgtg isaameilsq npvsvgisvm lgvgaiaahn aiesseqkrt llmkvfvknf ldqaatdelv kenpekiima lfeavqtign plrliyhlyg vyykgweake lsertagrnl ftlimfeafe llgmdsqgki rnlsgnyild liyglhkqin rglkkmvlgw apapfscdwt psderirlpt dnylrvetrc pcgyemkafk nvggkltkve esgpflcrnr pgrgpvnyrv tkyyddnlre ikpvaklegq vehyykgvta kidyskgkml latdkweveh gvitrlakry tgvgfngayl gdepnhralv erdcatitkn tvqflkmkkg caftydltis nltrlielvh rnnleekeip tatvttwlay tfvnedvgti kpvlgervip dpvvdinlqp evqvdtsevg itiigretlm ttgvtpvlek vepdasdnqn svkigldegn ypgpgiqtht lteeihnrda rpfimilgsr nsisnrakta rninlytgnd preirdlmaa grmlvvalrd vdpelsemvd fkgtfldrea lealslgqpk pkqvtkeavr nlieqkkdve ipnwfasddp vflevalknd kyylvgdvge lkdqakalga tdqtriikev gsrtyamkls swflkasnkq msltplfeel llrcppatks nkghmasayq laqgnweplg cgvhlgtipa rrvkihpyea ylklkdfiee eekkprvkdt virebnkwil kkirfqgnln tkkmlnpgkl seqldregrk rniynhqigt imssagirle klpivraqtd tktfheaird kidksenrqn pelhnkllei fhtiaqptlk htygevtweq leagvnrkga agflekknig evldsekhlv eqlvrdlkag rkikyyetai pknekrdvsd dwqagdlvve krprviqype aktrlaitkv mynwvkqqpv vipgyegktp lfnifdkvrk ewdsfnepva vsfdtkawdt qvtskdlqli geiqkyyykk ewhkfidtit dhmtevpvit adgevyirng qrgsgqpdts agnsmlnvlt mmygfcestg vpyksfnrva rihvcgddgf litekglglk fankgmqilh eagkpqkite gekmkvayrf ediefcshtp vpvrwsdnts shmagrdtav ilskmatrld ssgergttay ekavafsfll myswnplvrr icllvlsqqp etdpskhaty yykgdpigay kdvigrnlse lkrtgfekla nlnlslstlg vwtkhtskri iqdcvaigke egnwlvkpdr lissktghly ipdkgftlqg khyeqlqlrt etnpvmgvgt eryklgpivn lllrrlkill mtavgvss SEQ ID NO: 6
melitnelly ktykqkpvgv eepvydqagn plfgergaih pqstlklphk rgernvptsl aslpkrgdcr sgnskgpvsg iylkpgplfy qdykgpvyhr aplelfeegs mcettkrigr vtgsdgklyh iyicidgcit vksatrshqr vlrwvhnrld cplwvtscsd tkeegatkkk qqkpdrlekg rmkivpkese kdsktkppda tivvdgvkyq vkkkgkvksk ntqdglyhnk nkppesrkkl ekallawail avvlievtmg enitqwnlqd ngtegiqram fqrgvnrslh giwpekictg vpshlatdve lktihgmmda sektnytccr lqrhewnkhg wcnwyniepw ilimnrtqan ltegqpprec avtcrydrds dlnvvtqard sptpltgckk gknfsfagvl trgpcnfeia asdvlfkehe ctgvfqdtah ylvdgvtnsl esarqgtakl ttwlgkqlgi lgkklenksk twfgayaasp ycdvdrkigy iwftknctpa clpkntkiig pgkfdtnaed -continued

```
gkilhemggh lsevlllslv vlsdfapeta samylilhfa ipqshvditd cdktqlnlti
elttadvipg svwnlgkyvc irpdwwpyet aavlafeevg qvvkivlral rdltriwnaa
tttaflvcli kmvrgqvvqg ilwllllitgv qghldckpey syaiakndrv gplgaegltt
vwkdyshemk ledtmviawc kggkftylsr ctretrylai lhsralptsv vfkklfegqk
qedtvemddd fefglcpcda kpivrgkfnt tllngpafqm vcpigwtgtv scmlanrdtl
dtavvrtyrr svpfpyrqgc itqktlgedl ydcalggnwt cvtgdqsryt ggliesckwc
gykfqksegl phypigkcrl nnetgyrlvd dtscdregva ivphglvkck igdttvqvia
tdtklgpmpc kpheiisseg piektactfn ytrtlknkyf eprdsyfqqy mlkgdyqywf
dlevtdhhrd yfaesilvvv vallggryvl wllvtymvls eqkasgaqyg agevvmmgnl
lthdnvevvt yffllylllr eesvkkwvll lyhilvahpl ksvivillmi gdvvkadpgg
qgylgqidvc ftmvviiiig liiarrdpti vplitivasl rvtgltyspg vdaamaviti
tllmvsyvtd yfrykrwlqc ilslvsgvfl irclihlgri etpevtipnw rpltlilfyl
isttvvtmwk idlaglllqg vpilllittl wadfltlili lptyelvkly ylktiktdie
kswlggldyk rvdsiydvde sgegvylfps rqkaqknfsm llplvratli scvsskwqli
ymaylsvdfm yymhrkviee isggtnmisr ivaalielnw smeeeeskgl kkfyllsgrl
rnliikhkvr netvagwyge eevygmpkim tiikastlnk nkhciictvc egrkwkggtc
pkcgrhgkpi tcgmsladfe erhykrifir egnfegpfrq eyngfiqyta rgqlflrnlp
ilatkvkmlm vgnlgeevgd lehlgwilrg pavckkiteh erchinildk ltaffgimpr
gttprapvrf ptsllkvrrg letgwaythq ggissvdhvt agkdllvcds mgrtrvvcqs
nnkltdetey gvktdsgcpd garcyvlnpe avnisgskga vvhlqktgge ftcvtasgtp
affdlknlkg wsglpifeas sgrvvgrvkv gkneeskptk imsgiqtvsk ntadltemvk
kitsmnrgdf kqitlatgag kttelpkavi eeigrhkrvl vliplraaae svyqymrlkh
psiafnlrig dmkegdmatg ityasygyfc qmpqpklraa mveysyifld eyhcatpeql
aiigkihrfs esirvvamta tpagsvtttg qkhpieefia pevmegedlg sqfldiaglk
ipvdemkgnm lvfvptrnma vevakklkak gynsgyyysg edpanlrvvt sqspyvivat
naiesgvtlp dldtvvdtgl kcekrvrvss kipfivtglk rmavtvgeqa qrrgrvgrvk
pgryyrsqet atgskdyhyd llqaqrygie dginvtksfr emnydwslye edsllitqle
ilnnllised lpaavknima rtdhpepiql aynsyevqvp vlfpkirnge vtdtyenysf
lnarklgedv pvyiyatede dlavdllgld wpdpgnqqvv etgkalkqva glssaenall
valfgyvgyq alskrhvpmi tdiytiedqr ledtthlqya pnaiktegte telkelasgd
vekimgaisd yaaggldfvk sqaekiktap lfkenveaar gyvqklidsl iedkdviiry
glwgthtaly ksiaarlghe tafatlvlkw lafggetvsd hirqaavdlv vyyvmnkpsf
pgdtetqqeg rrfvaslfis alatytyktw nynnlskvve palaylpyat salkmftptr
lesvvilstt iyktylsirk gksdgllgtg isaameilsq npvsvgisvm lgvgaiaakm
aiesseqkrt llmkvfvknf ldqaatdelv kenpekiima lfeavqtign plrliyhlyg
vyykgweake lsertagrnl ftlimfeafe llgmdsegki rnlsgnyild lihglhkqin
rglkkivlgw apapfscdwt psderirlpt dsylrvetkc pcgyemkalk nvsgkltkve
esgpflcrnr pgrgpvnyrv tkyyddnlre irpvaklegq vehyykgvta ridyskgktl
latdkweveh gtltrltkry tgvgfrgayl gdepnhrdlv erdcatitkn tvqflkmkkg
caftydltis nltrlielvh rnnleekeip tatvttwlay tfvnedvgti kpvlgervip
```

-continued dpvvdinlqp evqvdtsevg itiigkeavm ttgvtpvmek vepdtdnnqs svkigldegn
ypgpgvqtht lveeihnkda rpfimvlgsk ssmsnrakta rninlytgnd preirdlmae
grilvvalrd idpdlselvd fkgtfldrea lealslgqpk pkqvtkaair dllkeerqve
ipdwftsddp vfldiamkkd kyhligdvve vkdqakalga tdqtrivkev gsrtytmkls
swflqasskq msltplfeel llrcppatks nkghmasayq laqgnweplg cgvhlgtvpa
rrvkmhpyea ylklkdlvee eekkprirdt virehnkwil kkikfggnln tkkmlnpgkl
seqldreghk rniynnqist vmssagirle klpivraqtd tksfheaird kidknenrqn
pelhnkllei fhtiadpslk htygevtweq leaginrkga agflekknig evldsekhlv
eqlvrdlkag rkiryyetai pknekrdvsd dwqagdlvde kkprviqype aktrlaitkv
mynwvkqqpv vipgyegktp lfnifnkvrk ewdlfnepva vsfdtkawdt qvtsrdlhli
geiqkyyyrk ewhkfidtit dhmvevpvit adgevyirng qrgsgqpdts agnsmlnvlt
miyafcestg vpyksfnrva kihvcgddgf litekglglk fsnkgmqilh eagkpqklte
gekmkvaykf ediefcshtp vpvrwsdnts symagrdtav ilskmatrld ssgergttay
ekavafsfll myswnplvrr icllvlsqrp etapstqtty yykgdpigay kdvigrnlse
lkrtgfekla nlnlslstlg iwtkhtskri iqdcvaigke egnwlvnadr lissktghly
ipdkgftlqg khyeqlqlga etnpvmgvgt eryklgpivn lllrrlkvll maavgass SEQ ID NO: 7
cgtggcttcttggtacggg SEQ ID NO: 8
agcggtatattgtacaaagcca SEQ ID NO: 9
tgcacgatctgtgaagggaaagaa SEQ ID NO: 10
tgcactgtatgtgagggccgagag

---

What is claimed is:

1. A vaccine comprising at least two live mutant viruses, of the same family, wherein each virus contains a mutation in the viral genome, and the mutations in the viruses reside in the same genomic site such that the mutant viruses cannot recombine with each other to eliminate the mutations, and wherein two of the live mutant viruses consist of a mutant Bovine Viral Diarrhea Virus Type 1 (BVDV-1) and a mutant Bovine Viral Diarrhea Virus Type 2 (BVDV-2), wherein the BVDV-1 and the BVDV-2 comprise a mutation comprising an insertion of a heterologous sequence in the NS2-3 region that results in a cytopathic biotype, wherein said heterologous sequence is inserted at 3' of nucleotide #4993 of the BVDV-1 genome, and at 3' of nucleotide #4993 of the BVDV-2 genome.

2. A vaccine comprising at least two live mutant viruses of the same family, wherein each virus contains a mutation in the viral genome, and the mutations in the viruses reside in the same genomic site such that the mutant viruses cannot recombine with each other to eliminate the mutations, and wherein two of the live mutant viruses consist of a mutant Bovine Viral Diarrhea Virus Type 1 (BVDV-1) and a mutant Bovine Viral Diarrhea Virus Type 2 (BVDV-2), wherein the BVDV-1 and the BVDV-2 comprise a mutation comprising an insertion of a heterologous sequence in the NS2-3 region that results in a cytopathic biotype, wherein said heterologous sequence is a DnaJ coding sequence or a portion thereof.

3. The vaccine of claim 2 wherein said DnaJ coding sequence or a portion thereof is inserted at 3' of nucleotide #4993 of the BVDV-1 genome, and at 3' of nucleotide #4993 of the BVDV-2 genome.

4. The vaccine of claim 3 wherein the cp BVDV-1 is BVDV-1 NADL, and the cp BVDV-2 is BVDV-2 53637.

5. A vaccine comprising at least two live mutant viruses of the same family, wherein each virus contains a mutation in the viral genome, and the mutations in the viruses reside in the same genomic site such that the mutant viruses cannot recombine with each other to eliminate the mutations, and wherein two of the live mutant viruses consist of a mutant cytopathic (cp) Bovine Viral Diarrhea Virus Type 1 (BVDV-1) and a mutant cp Bovine Viral Diarrhea Virus Type 2 (BVDV-2), and wherein the vaccine further comprises at least one of bovine herpesvirus-1, bovine respiratory syncytial virus, parainfluenza virus-3, *Campylobacter fetus, Leptospira canicola, Leptospira grippotyphosa, Leptospira hardjo, Leptospira icterohaemorrhagiae, Leptospira pomona,* or *Mannhemia haemolytica.*

* * * * *

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide forward primer
      53637U1

<400> SEQUENCE: 1
cgtccacaga tggtttggt                                                   19

<210> SEQ ID NO 2
<211> LENGTH: 22
<212> TYPE: DNA
<213> ORGANISM: Artificial Sequence
<220> FEATURE:
<223> OTHER INFORMATION: synthetic reverse primer 53637L

<400> SEQUENCE: 2
ggctatgtat tggacgtaac cc                                               22

<210> SEQ ID NO 3

```
<211> LENGTH: 670
<212> TYPE: DNA
<213> ORGANISM: Bovine Viral Diarrhea Virus 2 strain 53637

<400> SEQUENCE: 3
cgtccacaga tggtttggtg aggaggaaat atatggggca cccaaggtga tcaccatcat      60
aaaagctagt accctaagta aaaacaggca ctgcataatc tgcacgatct gtgaagggaa     120
agaatggaac ggagccaact gcccaaagtg tggaagacaa ggaaagccca taacatgtgg     180
aatgacactc gcagactttg aggagaaaca ttacaaaaag atatttataa gagaaggacg     240
ccaagaagca atgaatacga tgatgtgcag ccgatgccag ggaaagcata ggaggtttga     300
aacggaccgg gaacctaaga gtgccagata ctgtgctgag tgtaataggc tgcatcctgc     360
tgaggaaggt gacttttggg cagagtcaag catgttgggc tcaaaatca cctactttgc      420
gctgatggat ggaaaggtgt atgatatcac agagtgggct ggatgccagc gtgtgggaat     480
ctccccagat acccacagag tcccttgtca catctcattt ggttcacgga tgccaggcac     540
cagtgggcgg cagagagcta ctccagatgc ccctcctgct gaccttcagg atttcttgag     600
ccggatcttt caagtacccc caggccagat gtccagggaa gagtataagg gttacgtcca     660
atacatagcc                                                            670

<210> SEQ ID NO 4
<211> LENGTH: 12573
<212> TYPE: DNA
<213> ORGANISM: Bovine Viral Diarrhea Virus 1 strain NADL

<400> SEQUENCE: 4
gtatacgaga attagaaaag gcactcgtat acgtattggg caattaaaaa taataattag      60
gcctagggaa caaatccctc tcagcgaagg ccgaaaagag gctagccatg cccttagtag     120
gactagcata atgagggggg tagcaacagt ggtgagttcg ttggatggct taagccctga     180
gtacagggta gtcgtcagtg gttcgacgcc ttggaataaa ggtctcgaga tgccacgtgg     240
acgagggcat gcccaaagca catcttaacc tgagcggggg tcgcccaggt aaaagcagtt     300
ttaaccgact gttacgaata cagcctgata gggtgctgca gaggcccact gtattgctac     360
taaaaatctc tgctgtacat ggcacatgga gttgatcaca aatgaacttt tatacaaaac     420
atacaaacaa aaacccgtcg gggtggagga acctgtttat gatcaggcag gtgatccctt     480
atttggtgaa aggggagcag tccaccctca atcgacgcta agctcccac acaagagagg      540
ggaacgcgat gttccaacca acttggcatc cttaccaaaa agaggtgact gcaggtcggg     600
taatagcaga ggacctgtga gcgggatcta cctgaagcca gggccactat tttaccagga     660
ctataaaggt cccgtctatc acagggcccc gctggagctc tttgaggagg atccatgtg      720
tgaaacgact aaacggatag ggagagtaac tggaagtgac ggaaagctgt accacatttta    780
tgtgtgtata gatggatgta ataataaaa aagtgccacg agaagttacc aaagggtgtt     840
caggtgggtc cataataggc ttgactgccc tctatggtc acaacttgct cagacacgaa      900
agaagaggga gcaacaaaaa agaaaacaca gaaacccgac agactagaaa gggggaaaat     960
gaaaatagtg cccaaagaat ctgaaaaaga cagcaaaact aaacctcggg atgctacaat    1020
agtggtggaa ggagtcaaat accaggtgag gaagaaggga aaaaccaaga gtaaaaacac    1080
tcaggacggc ttgtaccata caaaaaacaa acctcaggaa tcacgcaaga aactggaaaa    1140
agcattgttg gcgtgggcaa taatagctat agttttgttt caagttacaa tgggagaaaa    1200
cataacacag tggaacctac aagataatgg gacggaaggg atacaacggg caatgttcca    1260
```

```
aagggdtgtg aatagaagtt tacatggaat ctggccagag aaaatctgta ctggcgtccc    1320
ttcccatcta gccaccgata tagaactaaa aacaattcat ggtatgatgg atgcaagtga    1380
gaagaccaac tacacgtgtt gcagacttca acgccatgag tggaacaagc atggttggtg    1440
caactggtac aatattgaac cctggattct agtcatgaat agaacccaag ccaatctcac    1500
tgagggacaa ccaccaaggg agtgcgcagt cacttgtagg tatgataggg ctagtgactt    1560
aaacgtggta acacaagcta gagatagccc cacaccctta acaggttgca agaaaggaaa    1620
gaacttctcc tttgcaggca tattgatgcg ggcccctgc aactttgaaa tagctgcaag    1680
tgatgtatta ttcaaagaac atgaacgcat tagtatgttc caggatacca ctctttacct    1740
tgttgacggg ttgaccaact ccttagaagg tgccagacaa ggaaccgcta aactgacaac    1800
ctggttaggc aagcagctcg ggatactagg aaaaaagttg gaaaacaaga gtaagacgtg    1860
gtttggagca tacgctgctt ccccttactg tgatgtcgat cgcaaaattg gctacatatg    1920
gtatacaaaa aattgcaccc ctgcctgctt acccaagaac acaaaaattg tcggccctgg    1980
gaaatttggc accaatgcag aggacggcaa gatattacat gagatggggg gtcacttgtc    2040
ggaggtacta ctactttctt tagtggtgct gtccgacttc gcaccggaaa cagctagtgt    2100
aatgtaccta atcctacatt tttccatccc acaaagtcac gttgatgtaa tggattgtga    2160
taagacccag ttgaacctca cagtggagct gacaacagct gaagtaatac cagggtcggt    2220
ctggaatcta ggcaaatatg tatgtataag accaaattgg tggccttatg agacaactgt    2280
agtgttggca tttgaagagg tgagccaggt ggtgaagtta tgttgagggg cactcagaga    2340
tttaacacgc atttggaacg ctgcaacaac tactgctttt ttagtatgcc ttgttaagat    2400
agtcaggggc cagatggtac agggcattct gtggctacta ttgataacag ggtacaagg    2460 gcacttggat tgcaaacctg aattctcgta tgccatagca aaggacgaaa gaattggtca    2520
actgggggct gaaggcctta ccaccacttg gaaggaatac tcacctggaa tgaagctgga    2580
agacacaatg gtcattgctt ggtgcgaaga tgggaagtta atgtacctcc aaagatgcac    2640
gagagaaacc agatatctcg caatcttgca tacaagagcc ttgccgacca gtgtggtatt    2700
caaaaaactc tttgatgggc gaaagcaaga ggatgtagtc gaaatgaacg acaactttga    2760
atttggactc tgcccatgtg atgccaaacc catagtaaga gggaagttca atacaacgct    2820
gctgaacgga ccggccttcc agatggtatg ccccatagga tggacaggga ctgtaagctg    2880
tacgtcattc aatatggaca ccttagccac aactgtggta cggacatata gaaggtctaa    2940
accattccct cataggcaag ctgtatcac ccaaaagaat ctgggggagg atctccataa    3000
ctgcatcctt ggaggaaatt ggactttgtgt gcctggagac caactactat acaaaggggg    3060
ctctattgaa tcttgcaagt ggtgtggcta tcaatttaaa gagagtgagg gactaccaca    3120
ctaccccatt ggcaagtgta aattggagaa cgagactggt tacaggctag tagacagtac    3180
ctcttgcaat agagaaggtg tggccatagt accacaaggg acattaaagt gcaagatagg    3240
aaaaacaact gtacaggtca tagctatgga taccaaactc ggacctatgc cttgcagacc    3300
atatgaaatc atatcaagtg aggggcctgt agaaaagaca gcgtgtactt tcaactacac    3360
taagacatta aaaaataagt attttgagcc cagagacagc tactttcagc aatacatgct    3420
aaaaggagag tatcaatact ggtttgacct ggaggtgact gaccatcacc gggattactt    3480
cgctgagtcc atattagtgg tggtagtagc cctcttgggt ggcagatatg tactttggtt    3540
actggttaca tacatggtct tatcagaaca gaaggcctta gggattcagt atggatcagg    3600
```

-continued

```
ggaagtggtg atgatgggca acttgctaac ccataacaat attgaagtgg tgacatactt    3660
cttgctgctg tacctactgc tgagggagga gagcgtaaag aagtgggtct tactcttata    3720
ccacatctta gtggtacacc caatcaaatc tgtaattgtg atcctactga tgattgggga    3780
tgtggtaaag gccgattcag ggggccaaga gtacttgggg aaaatagacc tctgttttac    3840
aacagtagta ctaatcgtca taggtttaat catagctagg cgtgacccaa ctatagtgcc    3900
actggtaaca ataatggcag cactgagggt cactgaactg acccaccagc tggagttga    3960 catcgctgtg gcggtcatga ctataaccct actgatggtt agctatgtga cagattattt    4020
tagatataaa aaatggttac agtgcattct cagcctggta tctgcggtgt tcttgataag    4080
aagcctaata tacctaggta gaatcgagat gccagaggta actatcccaa actggagacc    4140
actaacttta atactattat atttgatctc aacaacaatt gtaacgaggt ggaaggttga    4200
cgtggctggc ctattgttgc aatgtgtgcc tatcttattg ctggtcacaa ccttgtgggc    4260
cgacttctta accctaatac tgatcctgcc tacctatgaa ttggttaaat tatactatct    4320
gaaaactgtt aggactgata cagaaagaag ttggctaggg gggatagact atacaagagt    4380
tgactccatc tacgcgttg atgagagtgg agagggcgta tatcttttttc catcaaggca    4440 gaaagcacag gggaattttt ctatactctt gccccttatc aaagcaacac tgataagttg    4500
cgtcagcagt aaatggcagc taatatacat gagttactta actttggact ttatgtacta    4560
catgcacagg aaagttatag aagagatctc aggaggtacc aacataatat ccaggttagt    4620
ggcagcactc atagagctga actggtccat ggaagaagag gagagcaaag cttaaagaa    4680 gttttatcta ttgtctggaa ggttgagaaa cctaataata aaacataagg taaggaatga    4740
gaccgtggct tcttggtacg gggaggagga agtctacggt atgccaaaga tcatgactat    4800
aatcaaggcc agtacactga gtaagagcag gcactgcata atatgcactg tatgtgaggg    4860
ccgagagtgg aaaggtggca cctgcccaaa atgtggacgc catgggaagc cgataacgtg    4920
tgggatgtcg ctagcagatt ttgaagaaag acactataaa agaatctta taagggaagg    4980 caactttgag ggtatgtgca gccgatgcca gggaaagcat aggaggtttg aaatggaccg    5040
ggaacctaag agtgccagat actgtgctga gtgtaatagg ctgcatcctg ctgaggaagg    5100
tgacttttgg gcagagtcga gcatgttggg cctcaaaatc acctactttg cgctgatgga    5160
tggaaaggtg tatgatatca cagagtgggc tggatgccag cgtgtgggaa tctccccaga    5220
tacccacaga gtcccttgtc acatctcatt tggttcacgg atgcctttca ggcaggaata    5280
caatggcttt gtacaatata ccgctagggg gcaactattt ctgagaaact tgcccgtact    5340
ggcaactaaa gtaaaaatgc tcatggtagg caaccttgga gaagaaattg gtaatctgga    5400
acatcttggg tggatcctaa gggggcctgc cgtgtgtaag aagatcacag agcacgaaaa    5460
atgccacatt aatatactgg ataaactaac cgcatttttc gggatcatgc caaggggggac    5520 tacacccaga gccccggtga ggttccctac gagcttacta aaagtgagga ggggtctgga    5580
gactgcctgg gcttacacac accaaggcgg gataagttca gtcgaccatg taaccgccgg    5640
aaaagatcta ctggtctgtg acagcatggg acgaactaga gtggtttgcc aaaagcaacaa    5700 caggttgacc gatgagacag agtatggcgt caagactgac tcagggtgcc cagacggtgc    5760
cagatgttat gtgttaaatc cagaggccgt taacatatca ggatccaaag gggcagtcgt    5820
tcacctccaa aagacaggtg gagaattcac gtgtgtcacc gcatcaggca caccggcttt    5880
cttcgaccta aaaaacttga aaggatggtc aggcttgcct atatttgaag cctccagcgg    5940
gagggtggtt ggcagagtca aagtagggaa gaatgaagag tctaaaccta caaaaataat    6000
```

```
gagtggaatc cagaccgtct caaaaaacag agcagacctg accgagatgg tcaagaagat      6060
aaccagcatg aacaggggag acttcaagca gattactttg gcaacagggg caggcaaaac      6120
cacagaactc ccaaaagcag ttatagagga gataggaaga cacaagagag tattagttct      6180
tataccatta agggcagcgg cagagtcagt ctaccagtat atgagattga acacccaag       6240 catctctttt aacctaagga taggggacat gaaagagggg gacatggcaa ccgggataac      6300
ctatgcatca tacgggtact tctgccaaat gcctcaacca aagctcagag ctgctatggt      6360
agaatactca tacatattct tagatgaata ccattgtgcc actcctgaac aactggcaat      6420
tatcgggaag atccacagat tttcagagag tataagggtt gtcgccatga ctgccacgcc      6480
agcagggtcg gtgaccacaa caggtcaaaa gcacccaata gaggaattca tagcccccga      6540
ggtaatgaaa ggggaggatc ttggtagtca gttccttgat atagcagggt taaaaatacc      6600
agtggatgag atgaaaggca atatgttggt ttttgtacca acgagaaaca tggcagtaga      6660
ggtagcaaag aagctaaaag ctaagggcta taactctgga tactattaca gtggagagga      6720
tccagccaat ctgagagttg tgacatcaca atcccctat gtaatcgtgg ctacaaatgc       6780
tattgaatca ggagtgacac taccagattt ggacacggtt atagacacgg ggttgaaatg      6840
tgaaaagagg gtgagggtat catcaaagat acccttcatc gtaacaggcc ttaagaggat      6900
ggccgtgact gtgggtgagc aggcgcagcg taggggcaga gtaggtagag tgaaacccgg      6960
gaggtattat aggagccagg aaacagcaac agggtcaaag gactaccact atgacctctt      7020
gcaggcacaa agatacggga ttgaggatgg aatcaacgtg acgaaatcct ttagggagat      7080
gaattacgat tggagcctat acgaggagga cagcctacta ataacccagc tggaaatact      7140
aaataatcta ctcatctcag aagacttgcc agccgctgtt aagaacataa tggccaggac      7200
tgatcaccca gagccaatcc aacttgcata caacagctat gaagtccagg tcccggtcct      7260
attcccaaaa ataaggaatg gagaagtcac agacacctac gaaaattact cgtttctaaa      7320
tgccagaaag ttaggggagg atgtgcccgt gtatatctac gctactgaag atgaggatct      7380
ggcagttgac ctcttagggc tagactggcc tgatcctggg aaccagcagg tagtggagac      7440
tggtaaagca ctgaagcaag tgaccgggtt gtcctcggct gaaaatgccc tactagtggc      7500
tttatttggg tatgtgggtt accaggctct ctcaaagagg catgtcccaa tgataacaga      7560
catatatacc atcgaggacc agagactaga agacaccacc cacctccagt atgcacccaa      7620
cgccataaaa accgatggga cagagactga actgaaagaa ctggcgtcgg gtgacgtgga      7680
aaaaatcatg ggagccattt cagattatgc agctggggga ctggagtttg ttaaatccca      7740
agcagaaaag ataaaaacag ctccttttgtt taaagaaaac gcagaagccg caaaagggta      7800
tgtccaaaaa ttcattgact cattaattga aaataaagaa gaaataatca gatatggttt      7860
gtggggaaca cacacagcac tatacaaaag catagctgca agactggggc atgaaacagc      7920
gtttgccaca ctagtgttaa agtggctagc ttttggaggg gaatcagtgt cagaccacgt      7980
caagcaggcg gcagttgatt tagtggtcta ttatgtgatg aataagcctt ccttcccagg      8040
tgactccgag acacagcaag aagggaggcg attcgtcgca agcctgttca tctccgcact      8100
ggcaacctac acatacaaaa cttgaattaa ccacaatctc tctaaagtgg tggaaccagc      8160
cctggcttac ctcccctatg ctaccagcgc attaaaaatg ttcaccccaa cgcggctgga      8220
gagcgtggtg atactgagca ccacgatata taaaacatac ctctctataa ggaagggaa       8280 gagtgatgga ttgctgggta cggggataag tgcagccatg gaaatcctgt cacaaaaccc      8340
```

```
agtatcggta ggtatatctg tgatgttggg ggtaggggca atcgctgcgc acaacgctat    8400
tgagtccagt gaacagaaaa ggaccctact tatgaaggtg tttgtaaaga acttcttgga    8460
tcaggctgca acagatgagc tggtaaaaga aaacccagaa aaaattataa tggccttatt    8520
tgaagcagtc cagacaattg gtaacccccct gagactaata taccacctgt atggggttta   8580
ctacaaaggt tgggaggcca aggaactatc tgagaggaca gcaggcagaa acttattcac    8640
attgataatg tttgaagcct tcgagttatt agggatggac tcacaaggga aaataaggaa    8700
cctgtccgga aattacattt tggatttgat atacggccta cacaagcaaa tcaacagagg    8760
gctgaagaaa atggtactgg ggtgggcccc tgcacccttt agttgtgact ggaccccctag   8820
tgacgagagg atcagattgc caacagacaa ctatttgagg gtagaaacca ggtgcccatg    8880
tggctatgag atgaaagctt tcaaaaatgt aggtggcaaa cttaccaaag tggaggagag    8940
cgggcctttc ctatgtagaa acagacctgg taggggacca gtcaactaca gagtcaccaa    9000
gtattacgat gacaacctca gagagataaa accagtagca aagttggaag acaggtaga    9060
gcactactac aaaggggtca cagcaaaaat tgactacagt aaaggaaaaa tgctcttggc    9120
cactgacaag tgggaggtgg aacatggtgt cataaccagg ttagctaaga gatatactgg    9180
ggtcgggttc aatggtgcat acttaggtga cgagcccaat caccgtgctc tagtggagag    9240
ggactgtgca actataacca aaaacacagt acagtttcta aaaatgaaga aggggtgtgc    9300
gttcacctat gacctgacca tctccaatct gaccaggctc atcgaactag tacacaggaa    9360
caatcttgaa gagaaggaaa tacccaccgc tacggtcacc acatggctag cttacacctt    9420
cgtgaatgaa gacgtaggga ctataaaacc agtactagga gagagagtaa tccccgaccc    9480
tgtagttgat atcaatttac aaccagaggt gcaagtggac acgtcagagg ttgggatcac    9540
aataattgga agggaaaccc tgatgacaac gggagtgaca cctgtcttgg aaaaagtaga    9600
gcctgacgcc agcgacaacc aaaactcggt gaagatcggg ttggatgagg gtaattaccc    9660
agggcctgga atacagacac atacactaac agaagaaata cacaacaggg atgcgaggcc    9720
cttcatcatg atcctgggct caaggaattc catatcaaat agggcaaaga ctgctagaaa    9780
tataaatctg tacacaggaa atgaccccag ggaaatacga gacttgatgg ctgcagggcg    9840
catgttagta gtagcactga gggatgtcga ccctgagctg tctgaaatgg tcgatttcaa    9900
ggggactttt ttagataggg aggccctgga ggctctaagt ctcgggcaac ctaaaccgaa    9960
gcaggttacc aaggaagctg ttaggaattt gatagaacag aaaaaagatg tggagatccc   10020
taactggttt gcatcagatg acccagtatt tctggaagtg gccttaaaaa atgataagta   10080
ctacttagta ggagatgttg gagagctaaa agatcaagct aaagcacttg gggccacgga   10140
tcagacaaga attataaagg aggtaggctc aaggacgtat gccatgaagc tatctagctg   10200
gttcctcaag gcatcaaaca acagatgag tttaactcca ctgtttgagg aattgttgct    10260
acggtgccca cctgcaacta agagcaataa ggggcacatg gcatcagctt accaattggc   10320
acagggtaac tgggagcccc tcggttgcgg ggtgcaccta ggtacaatac agccagaag    10380
ggtgaagata cacccatatg aagcttacct gaagttgaaa gatttcatag aagaagaaga   10440
gaagaaacct agggttaagg atacagtaat aagagagcac aacaaatgga tacttaaaaa   10500
aataaggttt caaggaaacc tcaacaccaa gaaaatgctc aacccaggga actatctga    10560
acagttggac agggaggggc gcaagaggaa catctacaac caccagattg gtactataat   10620
gtcaagtgca ggcataaggc tggagaaatt gccaatagtg agggcccaaa ccgacaccaa   10680
aacctttcat gaggcaataa gagataagat agacaagagt gaaaaccggc aaaatccaga   10740
```

-continued

```
attgcacaac aaattgttgg agattttcca cacgatagcc caacccaccc tgaaacacac    10800
ctacggtgag gtgacgtggg agcaacttga ggcgggggta aatagaaagg gggcagcagg    10860
cttcctggag aagaagaaca tcggagaagt attggattca gaaaagcacc tggtagaaca    10920
attggtcagg gatctgaagg ccgggagaaa gataaaatat tatgaaactg caataccaaa    10980
aaatgagaag agagatgtca gtgatgactg gcaggcaggg gacctggtgg ttgagaagag    11040
gccaagagtt atccaatacc ctgaagccaa gacaaggcta gccatcacta aggtcatgta    11100
taactgggtg aaacagcagc ccgttgtgat tccaggatat gaaggaaaga ccccttgtt     11160
caacatcttt gataaagtga gaaggaatg ggactcgttc aatgagccag tggccgtaag    11220
ttttgacacc aaagcctggg acactcaagt gactagtaag gatctgcaac ttattggaga    11280
aatccagaaa tattactata agaaggagtg gcacaagttc attgacacca tcaccgacca    11340
catgacagaa gtaccagtta taacagcaga tggtgaagta tatataagaa atgggcagag    11400
agggagcggc cagccagaca caagtgctgg caacagcatg ttaaatgtcc tgacaatgat    11460
gtacggcttc tgcgaaagca caggggtacc gtacaagagt ttcaacaggg tggcaaggat    11520
ccacgtctgt ggggatgatg gcttcttaat aactgaaaaa gggttagggc tgaaatttgc    11580
taacaaaggg atgcagattc ttcatgaagc aggcaaacct cagaagataa cggaaggga    11640
aaagatgaaa gttgcctata gatttgagga tatagagttc tgttctcata ccccagtccc    11700
tgttaggtgg tccgacaaca ccagtagtca catggccggg agagacaccg ctgtgatact    11760
atcaaagatg gcaacaagat tggattcaag tggagagagg ggtaccacag catatgaaaa    11820
agcggtagcc ttcagtttct tgctgatgta ttcctggaac ccgcttgtta ggaggatttg    11880
cctgttggtc ctttcgcaac agccagagac agacccatca aaacatgcca cttattatta    11940
caaaggtgat ccaataggg cctataaaga tgtaataggt cggaatctaa gtgaactgaa    12000
gagaacaggc tttgagaaat tggcaaatct aaacctaagc ctgtccacgt gggggtctg    12060
gactaagcac acaagcaaaa gaataattca ggactgtgtt gccattggga agaagaggg    12120
caactggcta gttaagcccg acaggctgat atccagcaaa actggccact tatacatacc    12180
tgataaaggc tttacattac aaggaaagca ttatgagcaa ctgcagctaa gaacagagac    12240
aaacccggtc atggggttg ggactgagag atacaagtta ggtcccatag tcaatctgct    12300
gctgagaagg ttgaaaattc tgctcatgac ggccgtcggc gtcagcagct gagacaaaat    12360
gtatatattg taaataaatt aatccatgta catagtgtat ataaatatag ttgggaccgt    12420
ccacctcaag aagacgacac gcccaacacg cacagctaaa cagtagtcaa gattatctac    12480
ctcaagataa cactacattt aatgcacaca gcactttagc tgtatgagga tacgcccgac    12540
gtctatagtt ggactaggga agacctctaa cag                                12573
```

<210> SEQ ID NO 5
<211> LENGTH: 3988
<212> TYPE: PRT
<213> ORGANISM: Bovine Viral Diarrhea Virus 1 strain NADL

<400> SEQUENCE: 5

```
Met Glu Leu Ile Thr Asn Glu Leu Leu Tyr Lys Thr Tyr Lys Gln Lys
1               5                   10                  15

Pro Val Gly Val Glu Glu Pro Val Tyr Asp Gln Ala Gly Asp Pro Leu
            20                  25                  30

Phe Gly Glu Arg Gly Ala Val His Pro Gln Ser Thr Leu Lys Leu Pro
        35                  40                  45
```

```
His Lys Arg Gly Glu Arg Asp Val Pro Thr Asn Leu Ala Ser Leu Pro
 50                  55                  60
Lys Arg Gly Asp Cys Arg Ser Gly Asn Ser Arg Gly Pro Val Ser Gly
65                  70                  75                  80
Ile Tyr Leu Lys Pro Gly Pro Leu Phe Tyr Gln Asp Tyr Lys Gly Pro
                85                  90                  95
Val Tyr His Arg Ala Pro Leu Glu Leu Phe Glu Glu Gly Ser Met Cys
            100                 105                 110
Glu Thr Thr Lys Arg Ile Gly Arg Val Thr Gly Ser Asp Gly Lys Leu
        115                 120                 125
Tyr His Ile Tyr Val Cys Ile Asp Gly Cys Ile Ile Lys Ser Ala
    130                 135                 140
Thr Arg Ser Tyr Gln Arg Val Phe Arg Trp Val His Asn Arg Leu Asp
145                 150                 155                 160
Cys Pro Leu Trp Val Thr Thr Cys Ser Asp Thr Lys Glu Glu Gly Ala
                165                 170                 175
Thr Lys Lys Lys Thr Gln Lys Pro Asp Arg Leu Glu Arg Gly Lys Met
            180                 185                 190
Lys Ile Val Pro Lys Glu Ser Glu Lys Asp Ser Lys Thr Lys Pro Pro
        195                 200                 205
Asp Ala Thr Ile Val Val Glu Gly Val Lys Tyr Gln Val Arg Lys Lys
    210                 215                 220
Gly Lys Thr Lys Ser Lys Asn Thr Gln Asp Gly Leu Tyr His Asn Lys
225                 230                 235                 240
Asn Lys Pro Gln Glu Ser Arg Lys Lys Leu Glu Lys Ala Leu Leu Ala
                245                 250                 255
Trp Ala Ile Ile Ala Ile Val Leu Phe Gln Val Thr Met Gly Glu Asn
            260                 265                 270
Ile Thr Gln Trp Asn Leu Gln Asp Asn Gly Thr Glu Gly Ile Gln Arg
        275                 280                 285
Ala Met Phe Gln Arg Gly Val Asn Arg Ser Leu His Gly Ile Trp Pro
    290                 295                 300
Glu Lys Ile Cys Thr Gly Val Pro Ser His Leu Ala Thr Asp Ile Glu
305                 310                 315                 320
Leu Lys Thr Ile His Gly Met Met Asp Ala Ser Glu Lys Thr Asn Tyr
                325                 330                 335
Thr Cys Cys Arg Leu Gln Arg His Glu Trp Asn Lys His Gly Trp Cys
            340                 345                 350
Asn Trp Tyr Asn Ile Glu Pro Trp Ile Leu Val Met Asn Arg Thr Gln
        355                 360                 365
Ala Asn Leu Thr Glu Gly Gln Pro Pro Arg Glu Cys Ala Val Thr Cys
    370                 375                 380
Arg Tyr Asp Arg Ala Ser Asp Leu Asn Val Val Thr Gln Ala Arg Asp
385                 390                 395                 400
Ser Pro Thr Pro Leu Thr Gly Cys Lys Lys Gly Lys Asn Phe Ser Phe
                405                 410                 415
Ala Gly Ile Leu Met Arg Gly Pro Cys Asn Phe Glu Ile Ala Ala Ser
            420                 425                 430
Asp Val Leu Phe Lys Glu His Glu Arg Ile Ser Met Phe Gln Asp Thr
        435                 440                 445
Thr Leu Tyr Leu Val Asp Gly Leu Thr Asn Ser Leu Glu Gly Ala Arg
    450                 455                 460
```

```
Gln Gly Thr Ala Lys Leu Thr Thr Trp Leu Gly Lys Gln Leu Gly Ile
465                 470                 475                 480

Leu Gly Lys Lys Leu Glu Asn Lys Ser Lys Thr Trp Phe Gly Ala Tyr
                485                 490                 495

Ala Ala Ser Pro Tyr Cys Asp Val Asp Arg Lys Ile Gly Tyr Ile Trp
                500                 505                 510

Tyr Thr Lys Asn Cys Thr Pro Ala Cys Leu Pro Lys Asn Thr Lys Ile
            515                 520                 525

Val Gly Pro Gly Lys Phe Gly Thr Asn Ala Glu Asp Gly Lys Ile Leu
            530                 535                 540

His Glu Met Gly Gly His Leu Ser Glu Val Leu Leu Ser Leu Val
545                 550                 555                 560

Val Leu Ser Asp Phe Ala Pro Glu Thr Ala Ser Val Met Tyr Leu Ile
                565                 570                 575

Leu His Phe Ser Ile Pro Gln Ser His Val Asp Val Met Asp Cys Asp
                580                 585                 590

Lys Thr Gln Leu Asn Leu Thr Val Glu Leu Thr Thr Ala Glu Val Ile
            595                 600                 605

Pro Gly Ser Val Trp Asn Leu Gly Lys Tyr Val Cys Ile Arg Pro Asn
            610                 615                 620

Trp Trp Pro Tyr Glu Thr Thr Val Val Leu Ala Phe Glu Val Ser
625                 630                 635                 640

Gln Val Val Lys Leu Val Leu Arg Ala Leu Arg Asp Leu Thr Arg Ile
                645                 650                 655

Trp Asn Ala Ala Thr Thr Thr Ala Phe Leu Val Cys Leu Val Lys Ile
                660                 665                 670

Val Arg Gly Gln Met Val Gln Gly Ile Leu Trp Leu Leu Leu Ile Thr
            675                 680                 685

Gly Val Gln Gly His Leu Asp Cys Lys Pro Glu Phe Ser Tyr Ala Ile
            690                 695                 700

Ala Lys Asp Glu Arg Ile Gly Gln Leu Gly Ala Glu Gly Leu Thr Thr
705                 710                 715                 720

Thr Trp Lys Glu Tyr Ser Pro Gly Met Lys Leu Glu Asp Thr Met Val
                725                 730                 735

Ile Ala Trp Cys Glu Asp Gly Lys Leu Met Tyr Leu Gln Arg Cys Thr
                740                 745                 750

Arg Glu Thr Arg Tyr Leu Ala Ile Leu His Thr Arg Ala Leu Pro Thr
            755                 760                 765

Ser Val Val Phe Lys Lys Leu Phe Asp Gly Arg Lys Gln Glu Asp Val
            770                 775                 780

Val Glu Met Asn Asp Asn Phe Glu Phe Gly Leu Cys Pro Cys Asp Ala
785                 790                 795                 800

Lys Pro Ile Val Arg Gly Lys Phe Asn Thr Thr Leu Leu Asn Gly Pro
                805                 810                 815

Ala Phe Gln Met Val Cys Pro Ile Gly Trp Thr Gly Thr Val Ser Cys
                820                 825                 830

Thr Ser Phe Asn Met Asp Thr Leu Ala Thr Thr Val Val Arg Thr Tyr
            835                 840                 845

Arg Arg Ser Lys Pro Phe Pro His Arg Gln Gly Cys Ile Thr Gln Lys
            850                 855                 860

Asn Leu Gly Glu Asp Leu His Asn Cys Ile Leu Gly Gly Asn Trp Thr
865                 870                 875                 880

Cys Val Pro Gly Asp Gln Leu Leu Tyr Lys Gly Gly Ser Ile Glu Ser
```

-continued

```
                885                 890                 895
Cys Lys Trp Cys Gly Tyr Gln Phe Lys Glu Ser Glu Gly Leu Pro His
            900                 905                 910
Tyr Pro Ile Gly Lys Cys Lys Leu Glu Asn Glu Thr Gly Tyr Arg Leu
            915                 920                 925
Val Asp Ser Thr Ser Cys Asn Arg Glu Gly Val Ala Ile Val Pro Gln
            930                 935                 940
Gly Thr Leu Lys Cys Lys Ile Gly Lys Thr Thr Val Gln Val Ile Ala
945                 950                 955                 960
Met Asp Thr Lys Leu Gly Pro Met Pro Cys Arg Pro Tyr Glu Ile Ile
                965                 970                 975
Ser Ser Glu Gly Pro Val Glu Lys Thr Ala Cys Thr Phe Asn Tyr Thr
            980                 985                 990
Lys Thr Leu Lys Asn Lys Tyr Phe Glu Pro Arg Asp Ser Tyr Phe Gln
            995                 1000                1005
Gln Tyr Met Leu Lys Gly Glu Tyr Gln Tyr Trp Phe Asp Leu Glu
        1010                1015                1020
Val Thr Asp His His Arg Asp Tyr Phe Ala Glu Ser Ile Leu Val
        1025                1030                1035
Val Val Val Ala Leu Leu Gly Gly Arg Tyr Val Leu Trp Leu Leu
        1040                1045                1050
Val Thr Tyr Met Val Leu Ser Glu Gln Lys Ala Leu Gly Ile Gln
        1055                1060                1065
Tyr Gly Ser Gly Glu Val Val Met Met Gly Asn Leu Leu Thr His
        1070                1075                1080
Asn Asn Ile Glu Val Val Thr Tyr Phe Leu Leu Leu Tyr Leu Leu
        1085                1090                1095
Leu Arg Glu Glu Ser Val Lys Lys Trp Val Leu Leu Leu Tyr His
        1100                1105                1110
Ile Leu Val Val His Pro Ile Lys Ser Val Ile Val Ile Leu Leu
        1115                1120                1125
Met Ile Gly Asp Val Val Lys Ala Asp Ser Gly Gly Gln Glu Tyr
        1130                1135                1140
Leu Gly Lys Ile Asp Leu Cys Phe Thr Thr Val Leu Ile Val
        1145                1150                1155
Ile Gly Leu Ile Ile Ala Arg Arg Asp Pro Thr Ile Val Pro Leu
        1160                1165                1170
Val Thr Ile Met Ala Ala Leu Arg Val Thr Glu Leu Thr His Gln
        1175                1180                1185
Pro Gly Val Asp Ile Ala Val Ala Val Met Thr Ile Thr Leu Leu
        1190                1195                1200
Met Val Ser Tyr Val Thr Asp Tyr Phe Arg Tyr Lys Lys Trp Leu
        1205                1210                1215
Gln Cys Ile Leu Ser Leu Val Ser Ala Val Phe Leu Ile Arg Ser
        1220                1225                1230
Leu Ile Tyr Leu Gly Arg Ile Glu Met Pro Glu Val Thr Ile Pro
        1235                1240                1245
Asn Trp Arg Pro Leu Thr Leu Ile Leu Leu Tyr Leu Ile Ser Thr
        1250                1255                1260
Thr Ile Val Thr Arg Trp Lys Val Asp Val Ala Gly Leu Leu Leu
        1265                1270                1275
Gln Cys Val Pro Ile Leu Leu Leu Val Thr Leu Trp Ala Asp
        1280                1285                1290
```

```
Phe Leu Thr Leu Ile Leu Ile Leu Pro Thr Tyr Glu Leu Val Lys
1295                1300                1305

Leu Tyr Tyr Leu Lys Thr Val Arg Thr Asp Thr Glu Arg Ser Trp
1310                1315                1320

Leu Gly Gly Ile Asp Tyr Thr Arg Val Asp Ser Ile Tyr Asp Val
1325                1330                1335

Asp Glu Ser Gly Glu Gly Val Tyr Leu Phe Pro Ser Arg Gln Lys
1340                1345                1350

Ala Gln Gly Asn Phe Ser Ile Leu Leu Pro Leu Ile Lys Ala Thr
1355                1360                1365

Leu Ile Ser Cys Val Ser Ser Lys Trp Gln Leu Ile Tyr Met Ser
1370                1375                1380

Tyr Leu Thr Leu Asp Phe Met Tyr Tyr Met His Arg Lys Val Ile
1385                1390                1395

Glu Glu Ile Ser Gly Gly Thr Asn Ile Ile Ser Arg Leu Val Ala
1400                1405                1410

Ala Leu Ile Glu Leu Asn Trp Ser Met Glu Glu Glu Ser Lys
1415                1420                1425

Gly Leu Lys Lys Phe Tyr Leu Leu Ser Gly Arg Leu Arg Asn Leu
1430                1435                1440

Ile Ile Lys His Lys Val Arg Asn Glu Thr Val Ala Ser Trp Tyr
1445                1450                1455

Gly Glu Glu Glu Val Tyr Gly Met Pro Lys Ile Met Thr Ile Ile
1460                1465                1470

Lys Ala Ser Thr Leu Ser Lys Ser Arg His Cys Ile Ile Cys Thr
1475                1480                1485

Val Cys Glu Gly Arg Glu Trp Lys Gly Gly Thr Cys Pro Lys Cys
1490                1495                1500

Gly Arg His Gly Lys Pro Ile Thr Cys Gly Met Ser Leu Ala Asp
1505                1510                1515

Phe Glu Glu Arg His Tyr Lys Arg Ile Phe Ile Arg Glu Gly Asn
1520                1525                1530

Phe Glu Gly Met Cys Ser Arg Cys Gln Gly Lys His Arg Arg Phe
1535                1540                1545

Glu Met Asp Arg Glu Pro Lys Ser Ala Arg Tyr Cys Ala Glu Cys
1550                1555                1560

Asn Arg Leu His Pro Ala Glu Glu Gly Asp Phe Trp Ala Glu Ser
1565                1570                1575

Ser Met Leu Gly Leu Lys Ile Thr Tyr Phe Ala Leu Met Asp Gly
1580                1585                1590

Lys Val Tyr Asp Ile Thr Glu Trp Ala Gly Cys Gln Arg Val Gly
1595                1600                1605

Ile Ser Pro Asp Thr His Arg Val Pro Cys His Ile Ser Phe Gly
1610                1615                1620

Ser Arg Met Pro Phe Arg Gln Glu Tyr Asn Gly Phe Val Gln Tyr
1625                1630                1635

Thr Ala Arg Gly Gln Leu Phe Leu Arg Asn Leu Pro Val Leu Ala
1640                1645                1650

Thr Lys Val Lys Met Leu Met Val Gly Asn Leu Gly Glu Glu Ile
1655                1660                1665

Gly Asn Leu Glu His Leu Gly Trp Ile Leu Arg Gly Pro Ala Val
1670                1675                1680
```

-continued

```
Cys Lys Lys Ile Thr Glu His Glu Lys Cys His Ile Asn Ile Leu
1685                1690                1695

Asp Lys Leu Thr Ala Phe Phe Gly Ile Met Pro Arg Gly Thr Thr
1700                1705                1710

Pro Arg Ala Pro Val Arg Phe Pro Thr Ser Leu Leu Lys Val Arg
1715                1720                1725

Arg Gly Leu Glu Thr Ala Trp Ala Tyr Thr His Gln Gly Gly Ile
1730                1735                1740

Ser Ser Val Asp His Val Thr Ala Gly Lys Asp Leu Leu Val Cys
1745                1750                1755

Asp Ser Met Gly Arg Thr Arg Val Val Cys Gln Ser Asn Asn Arg
1760                1765                1770

Leu Thr Asp Glu Thr Glu Tyr Gly Val Lys Thr Asp Ser Gly Cys
1775                1780                1785

Pro Asp Gly Ala Arg Cys Tyr Val Leu Asn Pro Glu Ala Val Asn
1790                1795                1800

Ile Ser Gly Ser Lys Gly Ala Val Val His Leu Gln Lys Thr Gly
1805                1810                1815

Gly Glu Phe Thr Cys Val Thr Ala Ser Gly Thr Pro Ala Phe Phe
1820                1825                1830

Asp Leu Lys Asn Leu Lys Gly Trp Ser Gly Leu Pro Ile Phe Glu
1835                1840                1845

Ala Ser Ser Gly Arg Val Val Gly Arg Val Lys Val Gly Lys Asn
1850                1855                1860

Glu Glu Ser Lys Pro Thr Lys Ile Met Ser Gly Ile Gln Thr Val
1865                1870                1875

Ser Lys Asn Arg Ala Asp Leu Thr Glu Met Val Lys Lys Ile Thr
1880                1885                1890

Ser Met Asn Arg Gly Asp Phe Lys Gln Ile Thr Leu Ala Thr Gly
1895                1900                1905

Ala Gly Lys Thr Thr Glu Leu Pro Lys Ala Val Ile Glu Glu Ile
1910                1915                1920

Gly Arg His Lys Arg Val Leu Val Leu Ile Pro Leu Arg Ala Ala
1925                1930                1935

Ala Glu Ser Val Tyr Gln Tyr Met Arg Leu Lys His Pro Ser Ile
1940                1945                1950

Ser Phe Asn Leu Arg Ile Gly Asp Met Lys Glu Gly Asp Met Ala
1955                1960                1965

Thr Gly Ile Thr Tyr Ala Ser Tyr Gly Tyr Phe Cys Gln Met Pro
1970                1975                1980

Gln Pro Lys Leu Arg Ala Ala Met Val Glu Tyr Ser Tyr Ile Phe
1985                1990                1995

Leu Asp Glu Tyr His Cys Ala Thr Pro Glu Gln Leu Ala Ile Ile
2000                2005                2010

Gly Lys Ile His Arg Phe Ser Glu Ser Ile Arg Val Val Ala Met
2015                2020                2025

Thr Ala Thr Pro Ala Gly Ser Val Thr Thr Thr Gly Gln Lys His
2030                2035                2040

Pro Ile Glu Glu Phe Ile Ala Pro Glu Val Met Lys Gly Glu Asp
2045                2050                2055

Leu Gly Ser Gln Phe Leu Asp Ile Ala Gly Leu Lys Ile Pro Val
2060                2065                2070

Asp Glu Met Lys Gly Asn Met Leu Val Phe Val Pro Thr Arg Asn
```

-continued

```
            2075                2080                2085

Met Ala Val Glu Val Ala Lys Lys Leu Lys Ala Lys Gly Tyr Asn
        2090                2095                2100

Ser Gly Tyr Tyr Tyr Ser Gly Glu Asp Pro Ala Asn Leu Arg Val
        2105                2110                2115

Val Thr Ser Gln Ser Pro Tyr Val Ile Val Ala Thr Asn Ala Ile
        2120                2125                2130

Glu Ser Gly Val Thr Leu Pro Asp Leu Asp Thr Val Ile Asp Thr
        2135                2140                2145

Gly Leu Lys Cys Glu Lys Arg Val Arg Val Ser Ser Lys Ile Pro
        2150                2155                2160

Phe Ile Val Thr Gly Leu Lys Arg Met Ala Val Thr Val Gly Glu
        2165                2170                2175

Gln Ala Gln Arg Arg Gly Arg Val Gly Arg Val Lys Pro Gly Arg
        2180                2185                2190

Tyr Tyr Arg Ser Gln Glu Thr Ala Thr Gly Ser Lys Asp Tyr His
        2195                2200                2205

Tyr Asp Leu Leu Gln Ala Gln Arg Tyr Gly Ile Glu Asp Gly Ile
        2210                2215                2220

Asn Val Thr Lys Ser Phe Arg Glu Met Asn Tyr Asp Trp Ser Leu
        2225                2230                2235

Tyr Glu Glu Asp Ser Leu Leu Ile Thr Gln Leu Glu Ile Leu Asn
        2240                2245                2250

Asn Leu Leu Ile Ser Glu Asp Leu Pro Ala Ala Val Lys Asn Ile
        2255                2260                2265

Met Ala Arg Thr Asp His Pro Glu Pro Ile Gln Leu Ala Tyr Asn
        2270                2275                2280

Ser Tyr Glu Val Gln Val Pro Val Leu Phe Pro Lys Ile Arg Asn
        2285                2290                2295

Gly Glu Val Thr Asp Thr Tyr Glu Asn Tyr Ser Phe Leu Asn Ala
        2300                2305                2310

Arg Lys Leu Gly Glu Asp Val Pro Val Tyr Ile Tyr Ala Thr Glu
        2315                2320                2325

Asp Glu Asp Leu Ala Val Asp Leu Leu Gly Leu Asp Trp Pro Asp
        2330                2335                2340

Pro Gly Asn Gln Gln Val Val Glu Thr Gly Lys Ala Leu Lys Gln
        2345                2350                2355

Val Thr Gly Leu Ser Ser Ala Glu Asn Ala Leu Leu Val Ala Leu
        2360                2365                2370

Phe Gly Tyr Val Gly Tyr Gln Ala Leu Ser Lys Arg His Val Pro
        2375                2380                2385

Met Ile Thr Asp Ile Tyr Thr Ile Glu Asp Gln Arg Leu Glu Asp
        2390                2395                2400

Thr Thr His Leu Gln Tyr Ala Pro Asn Ala Ile Lys Thr Asp Gly
        2405                2410                2415

Thr Glu Thr Glu Leu Lys Glu Leu Ala Ser Gly Asp Val Glu Lys
        2420                2425                2430

Ile Met Gly Ala Ile Ser Asp Tyr Ala Ala Gly Gly Leu Glu Phe
        2435                2440                2445

Val Lys Ser Gln Ala Glu Lys Ile Lys Thr Ala Pro Leu Phe Lys
        2450                2455                2460

Glu Asn Ala Glu Ala Ala Lys Gly Tyr Val Gln Lys Phe Ile Asp
        2465                2470                2475
```

```
-continued

Ser Leu Ile Glu Asn Lys Glu Glu Ile Ile Arg Tyr Gly Leu Trp
    2480            2485                2490

Gly Thr His Thr Ala Leu Tyr Lys Ser Ile Ala Ala Arg Leu Gly
    2495            2500                2505

His Glu Thr Ala Phe Ala Thr Leu Val Leu Lys Trp Leu Ala Phe
    2510            2515                2520

Gly Gly Glu Ser Val Ser Asp His Val Lys Gln Ala Ala Val Asp
    2525            2530                2535

Leu Val Val Tyr Tyr Val Met Asn Lys Pro Ser Phe Pro Gly Asp
    2540            2545                2550

Ser Glu Thr Gln Gln Glu Gly Arg Arg Phe Val Ala Ser Leu Phe
    2555            2560                2565

Ile Ser Ala Leu Ala Thr Tyr Thr Tyr Lys Thr Trp Asn Tyr His
    2570            2575                2580

Asn Leu Ser Lys Val Val Glu Pro Ala Leu Ala Tyr Leu Pro Tyr
    2585            2590                2595

Ala Thr Ser Ala Leu Lys Met Phe Thr Pro Thr Arg Leu Glu Ser
    2600            2605                2610

Val Val Ile Leu Ser Thr Thr Ile Tyr Lys Thr Tyr Leu Ser Ile
    2615            2620                2625

Arg Lys Gly Lys Ser Asp Gly Leu Leu Gly Thr Gly Ile Ser Ala
    2630            2635                2640

Ala Met Glu Ile Leu Ser Gln Asn Pro Val Ser Val Gly Ile Ser
    2645            2650                2655

Val Met Leu Gly Val Gly Ala Ile Ala Ala His Asn Ala Ile Glu
    2660            2665                2670

Ser Ser Glu Gln Lys Arg Thr Leu Leu Met Lys Val Phe Val Lys
    2675            2680                2685

Asn Phe Leu Asp Gln Ala Ala Thr Asp Glu Leu Val Lys Glu Asn
    2690            2695                2700

Pro Glu Lys Ile Ile Met Ala Leu Phe Glu Ala Val Gln Thr Ile
    2705            2710                2715

Gly Asn Pro Leu Arg Leu Ile Tyr His Leu Tyr Gly Val Tyr Tyr
    2720            2725                2730

Lys Gly Trp Glu Ala Lys Glu Leu Ser Glu Arg Thr Ala Gly Arg
    2735            2740                2745

Asn Leu Phe Thr Leu Ile Met Phe Glu Ala Phe Glu Leu Leu Gly
    2750            2755                2760

Met Asp Ser Gln Gly Lys Ile Arg Asn Leu Ser Gly Asn Tyr Ile
    2765            2770                2775

Leu Asp Leu Ile Tyr Gly Leu His Lys Gln Ile Asn Arg Gly Leu
    2780            2785                2790

Lys Lys Met Val Leu Gly Trp Ala Pro Ala Pro Phe Ser Cys Asp
    2795            2800                2805

Trp Thr Pro Ser Asp Glu Arg Ile Arg Leu Pro Thr Asp Asn Tyr
    2810            2815                2820

Leu Arg Val Glu Thr Arg Cys Pro Cys Gly Tyr Glu Met Lys Ala
    2825            2830                2835

Phe Lys Asn Val Gly Gly Lys Leu Thr Lys Val Glu Glu Ser Gly
    2840            2845                2850

Pro Phe Leu Cys Arg Asn Arg Pro Gly Arg Gly Pro Val Asn Tyr
    2855            2860                2865
```

-continued

```
Arg Val Thr Lys Tyr Tyr Asp Asp Asn Leu Arg Glu  Ile Lys Pro
2870              2875              2880

Val Ala Lys Leu Glu Gly Gln Val Glu His Tyr Tyr  Lys Gly Val
2885              2890              2895

Thr Ala Lys Ile Asp Tyr Ser Lys Gly Lys Met Leu  Leu Ala Thr
2900              2905              2910

Asp Lys Trp Glu Val Glu His Gly Val Ile Thr Arg  Leu Ala Lys
2915              2920              2925

Arg Tyr Thr Gly Val Gly Phe Asn Gly Ala Tyr Leu  Gly Asp Glu
2930              2935              2940

Pro Asn His Arg Ala Leu Val Glu Arg Asp Cys Ala  Thr Ile Thr
2945              2950              2955

Lys Asn Thr Val Gln Phe Leu Lys Met Lys Lys Gly  Cys Ala Phe
2960              2965              2970

Thr Tyr Asp Leu Thr Ile Ser Asn Leu Thr Arg Leu  Ile Glu Leu
2975              2980              2985

Val His Arg Asn Asn Leu Glu Glu Lys Glu Ile Pro  Thr Ala Thr
2990              2995              3000

Val Thr Thr Trp Leu Ala Tyr Thr Phe Val Asn Glu  Asp Val Gly
3005              3010              3015

Thr Ile Lys Pro Val Leu Gly Glu Arg Val Ile Pro  Asp Pro Val
3020              3025              3030

Val Asp Ile Asn Leu Gln Pro Glu Val Gln Val Asp  Thr Ser Glu
3035              3040              3045

Val Gly Ile Thr Ile Ile Gly Arg Glu Thr Leu Met  Thr Thr Gly
3050              3055              3060

Val Thr Pro Val Leu Glu Lys Val Glu Pro Asp Ala  Ser Asp Asn
3065              3070              3075

Gln Asn Ser Val Lys Ile Gly Leu Asp Glu Gly Asn  Tyr Pro Gly
3080              3085              3090

Pro Gly Ile Gln Thr His Thr Leu Thr Glu Glu Ile  His Asn Arg
3095              3100              3105

Asp Ala Arg Pro Phe Ile Met Ile Leu Gly Ser Arg  Asn Ser Ile
3110              3115              3120

Ser Asn Arg Ala Lys Thr Ala Arg Asn Ile Asn Leu  Tyr Thr Gly
3125              3130              3135

Asn Asp Pro Arg Glu Ile Arg Asp Leu Met Ala Ala  Gly Arg Met
3140              3145              3150

Leu Val Val Ala Leu Arg Asp Val Asp Pro Glu Leu  Ser Glu Met
3155              3160              3165

Val Asp Phe Lys Gly Thr Phe Leu Asp Arg Glu Ala  Leu Glu Ala
3170              3175              3180

Leu Ser Leu Gly Gln Pro Lys Pro Lys Gln Val Thr  Lys Glu Ala
3185              3190              3195

Val Arg Asn Leu Ile Glu Gln Lys Lys Asp Val Glu  Ile Pro Asn
3200              3205              3210

Trp Phe Ala Ser Asp Asp Pro Val Phe Leu Glu Val  Ala Leu Lys
3215              3220              3225

Asn Asp Lys Tyr Tyr Leu Val Gly Asp Val Gly Glu  Leu Lys Asp
3230              3235              3240

Gln Ala Lys Ala Leu Gly Ala Thr Asp Gln Thr Arg  Ile Ile Lys
3245              3250              3255

Glu Val Gly Ser Arg Thr Tyr Ala Met Lys Leu Ser  Ser Trp Phe
```

-continued

```
         3260                3265                  3270

Leu Lys  Ala Ser Asn Lys Gln Met Ser Leu Thr Pro Leu Phe Glu
    3275                3280                  3285

Glu Leu  Leu Leu Arg Cys Pro Pro Ala Thr Lys Ser Asn Lys Gly
    3290                3295                  3300

His Met  Ala Ser Ala Tyr Gln Leu Ala Gln Gly Asn Trp Glu Pro
    3305                3310                  3315

Leu Gly  Cys Gly Val His Leu Gly Thr Ile Pro Ala Arg Arg Val
    3320                3325                  3330

Lys Ile  His Pro Tyr Glu Ala Tyr Leu Lys Leu Lys Asp Phe Ile
    3335                3340                  3345

Glu Glu  Glu Glu Lys Lys Pro Arg Val Lys Asp Thr Val Ile Arg
    3350                3355                  3360

Glu His  Asn Lys Trp Ile Leu Lys Lys Ile Arg Phe Gln Gly Asn
    3365                3370                  3375

Leu Asn  Thr Lys Lys Met Leu Asn Pro Gly Lys Leu Ser Glu Gln
    3380                3385                  3390

Leu Asp  Arg Glu Gly Arg Lys Arg Asn Ile Tyr Asn His Gln Ile
    3395                3400                  3405

Gly Thr  Ile Met Ser Ser Ala Gly Ile Arg Leu Glu Lys Leu Pro
    3410                3415                  3420

Ile Val  Arg Ala Gln Thr Asp Thr Lys Thr Phe His Glu Ala Ile
    3425                3430                  3435

Arg Asp  Lys Ile Asp Lys Ser Glu Asn Arg Gln Asn Pro Glu Leu
    3440                3445                  3450

His Asn  Lys Leu Leu Glu Ile Phe His Thr Ile Ala Gln Pro Thr
    3455                3460                  3465

Leu Lys  His Thr Tyr Gly Glu Val Thr Trp Glu Gln Leu Glu Ala
    3470                3475                  3480

Gly Val  Asn Arg Lys Gly Ala Ala Gly Phe Leu Glu Lys Lys Asn
    3485                3490                  3495

Ile Gly  Glu Val Leu Asp Ser Glu Lys His Leu Val Glu Gln Leu
    3500                3505                  3510

Val Arg  Asp Leu Lys Ala Gly Arg Lys Ile Lys Tyr Tyr Glu Thr
    3515                3520                  3525

Ala Ile  Pro Lys Asn Glu Lys Arg Asp Val Ser Asp Asp Trp Gln
    3530                3535                  3540

Ala Gly  Asp Leu Val Val Glu Lys Arg Pro Arg Val Ile Gln Tyr
    3545                3550                  3555

Pro Glu  Ala Lys Thr Arg Leu Ala Ile Thr Lys Val Met Tyr Asn
    3560                3565                  3570

Trp Val  Lys Gln Gln Pro Val Val Ile Pro Gly Tyr Glu Gly Lys
    3575                3580                  3585

Thr Pro  Leu Phe Asn Ile Phe Asp Lys Val Arg Lys Glu Trp Asp
    3590                3595                  3600

Ser Phe  Asn Glu Pro Val Ala Val Ser Phe Asp Thr Lys Ala Trp
    3605                3610                  3615

Asp Thr  Gln Val Thr Ser Lys Asp Leu Gln Leu Ile Gly Glu Ile
    3620                3625                  3630

Gln Lys  Tyr Tyr Tyr Lys Lys Glu Trp His Lys Phe Ile Asp Thr
    3635                3640                  3645

Ile Thr  Asp His Met Thr Glu Val Pro Val Ile Thr Ala Asp Gly
    3650                3655                  3660
```

Glu Val Tyr Ile Arg Asn Gly Gln Arg Gly Ser Gly Gln Pro Asp
    3665                3670                3675

Thr Ser Ala Gly Asn Ser Met Leu Asn Val Leu Thr Met Met Tyr
    3680                3685                3690

Gly Phe Cys Glu Ser Thr Gly Val Pro Tyr Lys Ser Phe Asn Arg
    3695                3700                3705

Val Ala Arg Ile His Val Cys Gly Asp Asp Gly Phe Leu Ile Thr
    3710                3715                3720

Glu Lys Gly Leu Gly Leu Lys Phe Ala Asn Lys Gly Met Gln Ile
    3725                3730                3735

Leu His Glu Ala Gly Lys Pro Gln Lys Ile Thr Glu Gly Glu Lys
    3740                3745                3750

Met Lys Val Ala Tyr Arg Phe Glu Asp Ile Glu Phe Cys Ser His
    3755                3760                3765

Thr Pro Val Pro Val Arg Trp Ser Asp Asn Thr Ser Ser His Met
    3770                3775                3780

Ala Gly Arg Asp Thr Ala Val Ile Leu Ser Lys Met Ala Thr Arg
    3785                3790                3795

Leu Asp Ser Ser Gly Glu Arg Gly Thr Thr Ala Tyr Glu Lys Ala
    3800                3805                3810

Val Ala Phe Ser Phe Leu Leu Met Tyr Ser Trp Asn Pro Leu Val
    3815                3820                3825

Arg Arg Ile Cys Leu Leu Val Leu Ser Gln Gln Pro Glu Thr Asp
    3830                3835                3840

Pro Ser Lys His Ala Thr Tyr Tyr Tyr Lys Gly Asp Pro Ile Gly
    3845                3850                3855

Ala Tyr Lys Asp Val Ile Gly Arg Asn Leu Ser Glu Leu Lys Arg
    3860                3865                3870

Thr Gly Phe Glu Lys Leu Ala Asn Leu Asn Leu Ser Leu Ser Thr
    3875                3880                3885

Leu Gly Val Trp Thr Lys His Thr Ser Lys Arg Ile Ile Gln Asp
    3890                3895                3900

Cys Val Ala Ile Gly Lys Glu Glu Gly Asn Trp Leu Val Lys Pro
    3905                3910                3915

Asp Arg Leu Ile Ser Ser Lys Thr Gly His Leu Tyr Ile Pro Asp
    3920                3925                3930

Lys Gly Phe Thr Leu Gln Gly Lys His Tyr Glu Gln Leu Gln Leu
    3935                3940                3945

Arg Thr Glu Thr Asn Pro Val Met Gly Val Gly Thr Glu Arg Tyr
    3950                3955                3960

Lys Leu Gly Pro Ile Val Asn Leu Leu Leu Arg Arg Leu Lys Ile
    3965                3970                3975

Leu Leu Met Thr Ala Val Gly Val Ser Ser
    3980                3985

<210> SEQ ID NO 6
<211> LENGTH: 3898
<212> TYPE: PRT
<213> ORGANISM: Bovine Viral Diarrhea Virus 1

<400> SEQUENCE: 6

Met Glu Leu Ile Thr Asn Glu Leu Leu Tyr Lys Thr Tyr Lys Gln Lys
1               5                   10                  15

Pro Val Gly Val Glu Glu Pro Val Tyr Asp Gln Ala Gly Asn Pro Leu

-continued

```
                    20                  25                  30
Phe Gly Glu Arg Gly Ala Ile His Pro Gln Ser Thr Leu Lys Leu Pro
                35                  40                  45
His Lys Arg Gly Glu Arg Asn Val Pro Thr Ser Leu Ala Ser Leu Pro
            50                  55                  60
Lys Arg Gly Asp Cys Arg Ser Gly Asn Ser Lys Gly Pro Val Ser Gly
65                  70                  75                  80
Ile Tyr Leu Lys Pro Gly Pro Leu Phe Tyr Gln Asp Tyr Lys Gly Pro
                85                  90                  95
Val Tyr His Arg Ala Pro Leu Glu Leu Phe Glu Glu Gly Ser Met Cys
            100                 105                 110
Glu Thr Thr Lys Arg Ile Gly Arg Val Thr Gly Ser Asp Gly Lys Leu
            115                 120                 125
Tyr His Ile Tyr Ile Cys Ile Asp Gly Cys Ile Thr Val Lys Ser Ala
            130                 135                 140
Thr Arg Ser His Gln Arg Val Leu Arg Trp Val His Asn Arg Leu Asp
145                 150                 155                 160
Cys Pro Leu Trp Val Thr Ser Cys Ser Asp Thr Lys Glu Glu Gly Ala
                165                 170                 175
Thr Lys Lys Gln Gln Lys Pro Asp Arg Leu Glu Lys Gly Arg Met
            180                 185                 190
Lys Ile Val Pro Lys Glu Ser Glu Lys Asp Ser Lys Thr Lys Pro Pro
            195                 200                 205
Asp Ala Thr Ile Val Val Asp Gly Val Lys Tyr Gln Val Lys Lys Lys
            210                 215                 220
Gly Lys Val Lys Ser Lys Asn Thr Gln Asp Gly Leu Tyr His Asn Lys
225                 230                 235                 240
Asn Lys Pro Pro Glu Ser Arg Lys Lys Leu Glu Lys Ala Leu Leu Ala
                245                 250                 255
Trp Ala Ile Leu Ala Val Val Leu Ile Glu Val Thr Met Gly Glu Asn
            260                 265                 270
Ile Thr Gln Trp Asn Leu Gln Asp Asn Gly Thr Glu Gly Ile Gln Arg
            275                 280                 285
Ala Met Phe Gln Arg Gly Val Asn Arg Ser Leu His Gly Ile Trp Pro
            290                 295                 300
Glu Lys Ile Cys Thr Gly Val Pro Ser His Leu Ala Thr Asp Val Glu
305                 310                 315                 320
Leu Lys Thr Ile His Gly Met Met Asp Ala Ser Glu Lys Thr Asn Tyr
                325                 330                 335
Thr Cys Cys Arg Leu Gln Arg His Glu Trp Asn Lys His Gly Trp Cys
            340                 345                 350
Asn Trp Tyr Asn Ile Glu Pro Trp Ile Leu Ile Met Asn Arg Thr Gln
            355                 360                 365
Ala Asn Leu Thr Glu Gly Gln Pro Pro Arg Glu Cys Ala Val Thr Cys
            370                 375                 380
Arg Tyr Asp Arg Asp Ser Asp Leu Asn Val Val Thr Gln Ala Arg Asp
385                 390                 395                 400
Ser Pro Thr Pro Leu Thr Gly Cys Lys Lys Gly Lys Asn Phe Ser Phe
                405                 410                 415
Ala Gly Val Leu Thr Arg Gly Pro Cys Asn Phe Glu Ile Ala Ala Ser
            420                 425                 430
Asp Val Leu Phe Lys Glu His Glu Cys Thr Gly Val Phe Gln Asp Thr
            435                 440                 445
```

```
Ala His Tyr Leu Val Asp Gly Val Thr Asn Ser Leu Glu Ser Ala Arg
    450                 455                 460

Gln Gly Thr Ala Lys Leu Thr Thr Trp Leu Gly Lys Gln Leu Gly Ile
465                 470                 475                 480

Leu Gly Lys Lys Leu Glu Asn Lys Ser Lys Thr Trp Phe Gly Ala Tyr
                485                 490                 495

Ala Ala Ser Pro Tyr Cys Asp Val Asp Arg Lys Ile Gly Tyr Ile Trp
            500                 505                 510

Phe Thr Lys Asn Cys Thr Pro Ala Cys Leu Pro Lys Asn Thr Lys Ile
        515                 520                 525

Ile Gly Pro Gly Lys Phe Asp Thr Asn Ala Glu Asp Gly Lys Ile Leu
    530                 535                 540

His Glu Met Gly Gly His Leu Ser Glu Val Leu Leu Ser Leu Val
545                 550                 555                 560

Val Leu Ser Asp Phe Ala Pro Glu Thr Ala Ser Ala Met Tyr Leu Ile
                565                 570                 575

Leu His Phe Ser Ile Pro Gln Ser His Val Asp Ile Thr Asp Cys Asp
            580                 585                 590

Lys Thr Gln Leu Asn Leu Thr Ile Glu Leu Thr Thr Ala Asp Val Ile
        595                 600                 605

Pro Gly Ser Val Trp Asn Leu Gly Lys Tyr Val Cys Ile Arg Pro Asp
    610                 615                 620

Trp Trp Pro Tyr Glu Thr Ala Ala Val Leu Ala Phe Glu Glu Val Gly
625                 630                 635                 640

Gln Val Val Lys Ile Val Leu Arg Ala Leu Arg Asp Leu Thr Arg Ile
                645                 650                 655

Trp Asn Ala Ala Thr Thr Thr Ala Phe Leu Val Cys Leu Ile Lys Met
            660                 665                 670

Val Arg Gly Gln Val Val Gln Gly Ile Leu Trp Leu Leu Leu Ile Thr
        675                 680                 685

Gly Val Gln Gly His Leu Asp Cys Lys Pro Glu Tyr Ser Tyr Ala Ile
    690                 695                 700

Ala Lys Asn Asp Arg Val Gly Pro Leu Gly Ala Glu Gly Leu Thr Thr
705                 710                 715                 720

Val Trp Lys Asp Tyr Ser His Glu Met Lys Leu Glu Asp Thr Met Val
                725                 730                 735

Ile Ala Trp Cys Lys Gly Gly Lys Phe Thr Tyr Leu Ser Arg Cys Thr
            740                 745                 750

Arg Glu Thr Arg Tyr Leu Ala Ile Leu His Ser Arg Ala Leu Pro Thr
        755                 760                 765

Ser Val Val Phe Lys Lys Leu Phe Glu Gly Gln Lys Gln Glu Asp Thr
    770                 775                 780

Val Glu Met Asp Asp Phe Glu Phe Gly Leu Cys Pro Cys Asp Ala
785                 790                 795                 800

Lys Pro Ile Val Arg Gly Lys Phe Asn Thr Thr Leu Leu Asn Gly Pro
                805                 810                 815

Ala Phe Gln Met Val Cys Pro Ile Gly Trp Thr Gly Thr Val Ser Cys
            820                 825                 830

Met Leu Ala Asn Arg Asp Thr Leu Asp Thr Ala Val Val Arg Thr Tyr
        835                 840                 845

Arg Arg Ser Val Pro Phe Pro Tyr Arg Gln Gly Cys Ile Thr Gln Lys
    850                 855                 860
```

```
Thr Leu Gly Glu Asp Leu Tyr Asp Cys Ala Leu Gly Gly Asn Trp Thr
865                 870                 875                 880

Cys Val Thr Gly Asp Gln Ser Arg Tyr Thr Gly Gly Leu Ile Glu Ser
            885                 890                 895

Cys Lys Trp Cys Gly Tyr Lys Phe Gln Lys Ser Glu Gly Leu Pro His
        900                 905                 910

Tyr Pro Ile Gly Lys Cys Arg Leu Asn Asn Glu Thr Gly Tyr Arg Leu
            915                 920                 925

Val Asp Asp Thr Ser Cys Asp Arg Glu Gly Val Ala Ile Val Pro His
        930                 935                 940

Gly Leu Val Lys Cys Lys Ile Gly Asp Thr Thr Val Gln Val Ile Ala
945                 950                 955                 960

Thr Asp Thr Lys Leu Gly Pro Met Pro Cys Lys Pro His Glu Ile Ile
            965                 970                 975

Ser Ser Glu Gly Pro Ile Glu Lys Thr Ala Cys Thr Phe Asn Tyr Thr
        980                 985                 990

Arg Thr Leu Lys Asn Lys Tyr Phe Glu Pro Arg Asp Ser Tyr Phe Gln
            995                 1000                1005

Gln Tyr Met Leu Lys Gly Asp Tyr Gln Tyr Trp Phe Asp Leu Glu
    1010                1015                1020

Val Thr Asp His His Arg Asp Tyr Phe Ala Glu Ser Ile Leu Val
    1025                1030                1035

Val Val Val Ala Leu Leu Gly Gly Arg Tyr Val Leu Trp Leu Leu
    1040                1045                1050

Val Thr Tyr Met Val Leu Ser Glu Gln Lys Ala Ser Gly Ala Gln
    1055                1060                1065

Tyr Gly Ala Gly Glu Val Val Met Met Gly Asn Leu Leu Thr His
    1070                1075                1080

Asp Asn Val Glu Val Val Thr Tyr Phe Phe Leu Leu Tyr Leu Leu
    1085                1090                1095

Leu Arg Glu Glu Ser Val Lys Lys Trp Val Leu Leu Leu Tyr His
    1100                1105                1110

Ile Leu Val Ala His Pro Leu Lys Ser Val Ile Val Ile Leu Leu
    1115                1120                1125

Met Ile Gly Asp Val Val Lys Ala Asp Pro Gly Gly Gln Gly Tyr
    1130                1135                1140

Leu Gly Gln Ile Asp Val Cys Phe Thr Met Val Val Ile Ile Ile
    1145                1150                1155

Ile Gly Leu Ile Ile Ala Arg Arg Asp Pro Thr Ile Val Pro Leu
    1160                1165                1170

Ile Thr Ile Val Ala Ser Leu Arg Val Thr Gly Leu Thr Tyr Ser
    1175                1180                1185

Pro Gly Val Asp Ala Ala Met Ala Val Ile Thr Ile Thr Leu Leu
    1190                1195                1200

Met Val Ser Tyr Val Thr Asp Tyr Phe Arg Tyr Lys Arg Trp Leu
    1205                1210                1215

Gln Cys Ile Leu Ser Leu Val Ser Gly Val Phe Leu Ile Arg Cys
    1220                1225                1230

Leu Ile His Leu Gly Arg Ile Glu Thr Pro Glu Val Thr Ile Pro
    1235                1240                1245

Asn Trp Arg Pro Leu Thr Leu Ile Leu Phe Tyr Leu Ile Ser Thr
    1250                1255                1260

Thr Val Val Thr Met Trp Lys Ile Asp Leu Ala Gly Leu Leu Leu
```

-continued

```
             1265                1270                1275
Gln Gly Val Pro Ile Leu Leu Leu Ile Thr Thr Leu Trp Ala Asp
    1280                1285                1290

Phe Leu Thr Leu Ile Leu Ile Leu Pro Thr Tyr Glu Leu Val Lys
    1295                1300                1305

Leu Tyr Tyr Leu Lys Thr Ile Lys Thr Asp Ile Glu Lys Ser Trp
    1310                1315                1320

Leu Gly Gly Leu Asp Tyr Lys Arg Val Asp Ser Ile Tyr Asp Val
    1325                1330                1335

Asp Glu Ser Gly Glu Gly Val Tyr Leu Phe Pro Ser Arg Gln Lys
    1340                1345                1350

Ala Gln Lys Asn Phe Ser Met Leu Leu Pro Leu Val Arg Ala Thr
    1355                1360                1365

Leu Ile Ser Cys Val Ser Ser Lys Trp Gln Leu Ile Tyr Met Ala
    1370                1375                1380

Tyr Leu Ser Val Asp Phe Met Tyr Tyr Met His Arg Lys Val Ile
    1385                1390                1395

Glu Glu Ile Ser Gly Gly Thr Asn Met Ile Ser Arg Ile Val Ala
    1400                1405                1410

Ala Leu Ile Glu Leu Asn Trp Ser Met Glu Glu Glu Glu Ser Lys
    1415                1420                1425

Gly Leu Lys Lys Phe Tyr Leu Leu Ser Gly Arg Leu Arg Asn Leu
    1430                1435                1440

Ile Ile Lys His Lys Val Arg Asn Glu Thr Val Ala Gly Trp Tyr
    1445                1450                1455

Gly Glu Glu Glu Val Tyr Gly Met Pro Lys Ile Met Thr Ile Ile
    1460                1465                1470

Lys Ala Ser Thr Leu Asn Lys Asn Lys His Cys Ile Ile Cys Thr
    1475                1480                1485

Val Cys Glu Gly Arg Lys Trp Lys Gly Gly Thr Cys Pro Lys Cys
    1490                1495                1500

Gly Arg His Gly Lys Pro Ile Thr Cys Gly Met Ser Leu Ala Asp
    1505                1510                1515

Phe Glu Glu Arg His Tyr Lys Arg Ile Phe Ile Arg Glu Gly Asn
    1520                1525                1530

Phe Glu Gly Pro Phe Arg Gln Glu Tyr Asn Gly Phe Ile Gln Tyr
    1535                1540                1545

Thr Ala Arg Gly Gln Leu Phe Leu Arg Asn Leu Pro Ile Leu Ala
    1550                1555                1560

Thr Lys Val Lys Met Leu Met Val Gly Asn Leu Gly Glu Glu Val
    1565                1570                1575

Gly Asp Leu Glu His Leu Gly Trp Ile Leu Arg Gly Pro Ala Val
    1580                1585                1590

Cys Lys Lys Ile Thr Glu His Glu Arg Cys His Ile Asn Ile Leu
    1595                1600                1605

Asp Lys Leu Thr Ala Phe Phe Gly Ile Met Pro Arg Gly Thr Thr
    1610                1615                1620

Pro Arg Ala Pro Val Arg Phe Pro Thr Ser Leu Leu Lys Val Arg
    1625                1630                1635

Arg Gly Leu Glu Thr Gly Trp Ala Tyr Thr His Gln Gly Gly Ile
    1640                1645                1650

Ser Ser Val Asp His Val Thr Ala Gly Lys Asp Leu Leu Val Cys
    1655                1660                1665
```

-continued

```
Asp Ser Met Gly Arg Thr Arg Val Val Cys Gln Ser Asn Asn Lys
    1670            1675                1680

Leu Thr Asp Glu Thr Glu Tyr Gly Val Lys Thr Asp Ser Gly Cys
    1685            1690                1695

Pro Asp Gly Ala Arg Cys Tyr Val Leu Asn Pro Glu Ala Val Asn
    1700            1705                1710

Ile Ser Gly Ser Lys Gly Ala Val Val His Leu Gln Lys Thr Gly
    1715            1720                1725

Gly Glu Phe Thr Cys Val Thr Ala Ser Gly Thr Pro Ala Phe Phe
    1730            1735                1740

Asp Leu Lys Asn Leu Lys Gly Trp Ser Gly Leu Pro Ile Phe Glu
    1745            1750                1755

Ala Ser Gly Arg Val Val Gly Arg Val Lys Val Gly Lys Asn
    1760            1765                1770

Glu Glu Ser Lys Pro Thr Lys Ile Met Ser Gly Ile Gln Thr Val
    1775            1780                1785

Ser Lys Asn Thr Ala Asp Leu Thr Glu Met Val Lys Lys Ile Thr
    1790            1795                1800

Ser Met Asn Arg Gly Asp Phe Lys Gln Ile Thr Leu Ala Thr Gly
    1805            1810                1815

Ala Gly Lys Thr Thr Glu Leu Pro Lys Ala Val Ile Glu Glu Ile
    1820            1825                1830

Gly Arg His Lys Arg Val Leu Val Leu Ile Pro Leu Arg Ala Ala
    1835            1840                1845

Ala Glu Ser Val Tyr Gln Tyr Met Arg Leu Lys His Pro Ser Ile
    1850            1855                1860

Ser Phe Asn Leu Arg Ile Gly Asp Met Lys Glu Gly Asp Met Ala
    1865            1870                1875

Thr Gly Ile Thr Tyr Ala Ser Tyr Gly Tyr Phe Cys Gln Met Pro
    1880            1885                1890

Gln Pro Lys Leu Arg Ala Ala Met Val Glu Tyr Ser Tyr Ile Phe
    1895            1900                1905

Leu Asp Glu Tyr His Cys Ala Thr Pro Glu Gln Leu Ala Ile Ile
    1910            1915                1920

Gly Lys Ile His Arg Phe Ser Glu Ser Ile Arg Val Val Ala Met
    1925            1930                1935

Thr Ala Thr Pro Ala Gly Ser Val Thr Thr Thr Gly Gln Lys His
    1940            1945                1950

Pro Ile Glu Glu Phe Ile Ala Pro Glu Val Met Glu Gly Glu Asp
    1955            1960                1965

Leu Gly Ser Gln Phe Leu Asp Ile Ala Gly Leu Lys Ile Pro Val
    1970            1975                1980

Asp Glu Met Lys Gly Asn Met Leu Val Phe Val Pro Thr Arg Asn
    1985            1990                1995

Met Ala Val Glu Val Ala Lys Lys Leu Lys Ala Lys Gly Tyr Asn
    2000            2005                2010

Ser Gly Tyr Tyr Tyr Ser Gly Glu Asp Pro Ala Asn Leu Arg Val
    2015            2020                2025

Val Thr Ser Gln Ser Pro Tyr Val Ile Val Ala Thr Asn Ala Ile
    2030            2035                2040

Glu Ser Gly Val Thr Leu Pro Asp Leu Asp Thr Val Val Asp Thr
    2045            2050                2055
```

-continued

```
Gly Leu Lys Cys Glu Lys Arg Val Arg Val Ser Ser Lys Ile Pro
    2060                2065                2070

Phe Ile Val Thr Gly Leu Lys Arg Met Ala Val Thr Val Gly Glu
    2075                2080                2085

Gln Ala Gln Arg Arg Gly Arg Val Gly Arg Val Lys Pro Gly Arg
    2090                2095                2100

Tyr Tyr Arg Ser Gln Glu Thr Ala Thr Gly Ser Lys Asp Tyr His
    2105                2110                2115

Tyr Asp Leu Leu Gln Ala Gln Arg Tyr Gly Ile Glu Asp Gly Ile
    2120                2125                2130

Asn Val Thr Lys Ser Phe Arg Glu Met Asn Tyr Asp Trp Ser Leu
    2135                2140                2145

Tyr Glu Glu Asp Ser Leu Leu Ile Thr Gln Leu Glu Ile Leu Asn
    2150                2155                2160

Asn Leu Leu Ile Ser Glu Asp Leu Pro Ala Ala Val Lys Asn Ile
    2165                2170                2175

Met Ala Arg Thr Asp His Pro Glu Pro Ile Gln Leu Ala Tyr Asn
    2180                2185                2190

Ser Tyr Glu Val Gln Val Pro Val Leu Phe Pro Lys Ile Arg Asn
    2195                2200                2205

Gly Glu Val Thr Asp Thr Tyr Glu Asn Tyr Ser Phe Leu Asn Ala
    2210                2215                2220

Arg Lys Leu Gly Glu Asp Val Pro Val Tyr Ile Tyr Ala Thr Glu
    2225                2230                2235

Asp Glu Asp Leu Ala Val Asp Leu Leu Gly Leu Asp Trp Pro Asp
    2240                2245                2250

Pro Gly Asn Gln Gln Val Val Glu Thr Gly Lys Ala Leu Lys Gln
    2255                2260                2265

Val Ala Gly Leu Ser Ser Ala Glu Asn Ala Leu Leu Val Ala Leu
    2270                2275                2280

Phe Gly Tyr Val Gly Tyr Gln Ala Leu Ser Lys Arg His Val Pro
    2285                2290                2295

Met Ile Thr Asp Ile Tyr Thr Ile Glu Asp Gln Arg Leu Glu Asp
    2300                2305                2310

Thr Thr His Leu Gln Tyr Ala Pro Asn Ala Ile Lys Thr Glu Gly
    2315                2320                2325

Thr Glu Thr Glu Leu Lys Glu Leu Ala Ser Gly Asp Val Glu Lys
    2330                2335                2340

Ile Met Gly Ala Ile Ser Asp Tyr Ala Ala Gly Gly Leu Asp Phe
    2345                2350                2355

Val Lys Ser Gln Ala Glu Lys Ile Lys Thr Ala Pro Leu Phe Lys
    2360                2365                2370

Glu Asn Val Glu Ala Ala Arg Gly Tyr Val Gln Lys Leu Ile Asp
    2375                2380                2385

Ser Leu Ile Glu Asp Lys Asp Val Ile Ile Arg Tyr Gly Leu Trp
    2390                2395                2400

Gly Thr His Thr Ala Leu Tyr Lys Ser Ile Ala Ala Arg Leu Gly
    2405                2410                2415

His Glu Thr Ala Phe Ala Thr Leu Val Leu Lys Trp Leu Ala Phe
    2420                2425                2430

Gly Gly Glu Thr Val Ser Asp His Ile Arg Gln Ala Ala Val Asp
    2435                2440                2445

Leu Val Val Tyr Tyr Val Met Asn Lys Pro Ser Phe Pro Gly Asp
```

-continued

| | | | | | | | | | | |
|---|---|---|---|---|---|---|---|---|---|---|
| | 2450 | | | 2455 | | | 2460 | | | |
| Thr | Glu | Thr | Gln | Gln | Glu | Gly | Arg | Arg | Phe | Val | Ala | Ser | Leu | Phe |
| | 2465 | | | | 2470 | | | | 2475 | |
| Ile | Ser | Ala | Leu | Ala | Thr | Tyr | Thr | Tyr | Lys | Thr | Trp | Asn | Tyr | Asn |
| | 2480 | | | | 2485 | | | | 2490 | |
| Asn | Leu | Ser | Lys | Val | Val | Glu | Pro | Ala | Leu | Ala | Tyr | Leu | Pro | Tyr |
| | 2495 | | | | 2500 | | | | 2505 | |
| Ala | Thr | Ser | Ala | Leu | Lys | Met | Phe | Thr | Pro | Thr | Arg | Leu | Glu | Ser |
| | 2510 | | | | 2515 | | | | 2520 | |
| Val | Val | Ile | Leu | Ser | Thr | Thr | Ile | Tyr | Lys | Thr | Tyr | Leu | Ser | Ile |
| | 2525 | | | | 2530 | | | | 2535 | |
| Arg | Lys | Gly | Lys | Ser | Asp | Gly | Leu | Leu | Gly | Thr | Gly | Ile | Ser | Ala |
| | 2540 | | | | 2545 | | | | 2550 | |
| Ala | Met | Glu | Ile | Leu | Ser | Gln | Asn | Pro | Val | Ser | Val | Gly | Ile | Ser |
| | 2555 | | | | 2560 | | | | 2565 | |
| Val | Met | Leu | Gly | Val | Gly | Ala | Ile | Ala | Ala | His | Asn | Ala | Ile | Glu |
| | 2570 | | | | 2575 | | | | 2580 | |
| Ser | Ser | Glu | Gln | Lys | Arg | Thr | Leu | Leu | Met | Lys | Val | Phe | Val | Lys |
| | 2585 | | | | 2590 | | | | 2595 | |
| Asn | Phe | Leu | Asp | Gln | Ala | Ala | Thr | Asp | Glu | Leu | Val | Lys | Glu | Asn |
| | 2600 | | | | 2605 | | | | 2610 | |
| Pro | Glu | Lys | Ile | Ile | Met | Ala | Leu | Phe | Glu | Ala | Val | Gln | Thr | Ile |
| | 2615 | | | | 2620 | | | | 2625 | |
| Gly | Asn | Pro | Leu | Arg | Leu | Ile | Tyr | His | Leu | Tyr | Gly | Val | Tyr | Tyr |
| | 2630 | | | | 2635 | | | | 2640 | |
| Lys | Gly | Trp | Glu | Ala | Lys | Glu | Leu | Ser | Glu | Arg | Thr | Ala | Gly | Arg |
| | 2645 | | | | 2650 | | | | 2655 | |
| Asn | Leu | Phe | Thr | Leu | Ile | Met | Phe | Glu | Ala | Phe | Glu | Leu | Leu | Gly |
| | 2660 | | | | 2665 | | | | 2670 | |
| Met | Asp | Ser | Glu | Gly | Lys | Ile | Arg | Asn | Leu | Ser | Gly | Asn | Tyr | Ile |
| | 2675 | | | | 2680 | | | | 2685 | |
| Leu | Asp | Leu | Ile | His | Gly | Leu | His | Lys | Gln | Ile | Asn | Arg | Gly | Leu |
| | 2690 | | | | 2695 | | | | 2700 | |
| Lys | Lys | Ile | Val | Leu | Gly | Trp | Ala | Pro | Ala | Pro | Phe | Ser | Cys | Asp |
| | 2705 | | | | 2710 | | | | 2715 | |
| Trp | Thr | Pro | Ser | Asp | Glu | Arg | Ile | Arg | Leu | Pro | Thr | Asp | Ser | Tyr |
| | 2720 | | | | 2725 | | | | 2730 | |
| Leu | Arg | Val | Glu | Thr | Lys | Cys | Pro | Cys | Gly | Tyr | Glu | Met | Lys | Ala |
| | 2735 | | | | 2740 | | | | 2745 | |
| Leu | Lys | Asn | Val | Ser | Gly | Lys | Leu | Thr | Lys | Val | Glu | Glu | Ser | Gly |
| | 2750 | | | | 2755 | | | | 2760 | |
| Pro | Phe | Leu | Cys | Arg | Asn | Arg | Pro | Gly | Arg | Gly | Pro | Val | Asn | Tyr |
| | 2765 | | | | 2770 | | | | 2775 | |
| Arg | Val | Thr | Lys | Tyr | Tyr | Asp | Asp | Asn | Leu | Arg | Glu | Ile | Arg | Pro |
| | 2780 | | | | 2785 | | | | 2790 | |
| Val | Ala | Lys | Leu | Glu | Gly | Gln | Val | Glu | His | Tyr | Tyr | Lys | Gly | Val |
| | 2795 | | | | 2800 | | | | 2805 | |
| Thr | Ala | Arg | Ile | Asp | Tyr | Ser | Lys | Gly | Lys | Thr | Leu | Leu | Ala | Thr |
| | 2810 | | | | 2815 | | | | 2820 | |
| Asp | Lys | Trp | Glu | Val | Glu | His | Gly | Thr | Leu | Thr | Arg | Leu | Thr | Lys |
| | 2825 | | | | 2830 | | | | 2835 | |
| Arg | Tyr | Thr | Gly | Val | Gly | Phe | Arg | Gly | Ala | Tyr | Leu | Gly | Asp | Glu |
| | 2840 | | | | 2845 | | | | 2850 | |

```
Pro Asn His Arg Asp Leu Val Glu Arg Asp Cys Ala Thr Ile Thr
2855                 2860                2865

Lys Asn Thr Val Gln Phe Leu Lys Met Lys Lys Gly Cys Ala Phe
2870                 2875                2880

Thr Tyr Asp Leu Thr Ile Ser Asn Leu Thr Arg Leu Ile Glu Leu
2885                 2890                2895

Val His Arg Asn Asn Leu Glu Glu Lys Glu Ile Pro Thr Ala Thr
2900                 2905                2910

Val Thr Thr Trp Leu Ala Tyr Thr Phe Val Asn Glu Asp Val Gly
2915                 2920                2925

Thr Ile Lys Pro Val Leu Gly Glu Arg Val Ile Pro Asp Pro Val
2930                 2935                2940

Val Asp Ile Asn Leu Gln Pro Glu Val Gln Val Asp Thr Ser Glu
2945                 2950                2955

Val Gly Ile Thr Ile Ile Gly Lys Glu Ala Val Met Thr Thr Gly
2960                 2965                2970

Val Thr Pro Val Met Glu Lys Val Glu Pro Asp Thr Asp Asn Asn
2975                 2980                2985

Gln Ser Ser Val Lys Ile Gly Leu Asp Glu Gly Asn Tyr Pro Gly
2990                 2995                3000

Pro Gly Val Gln Thr His Thr Leu Val Glu Glu Ile His Asn Lys
3005                 3010                3015

Asp Ala Arg Pro Phe Ile Met Val Leu Gly Ser Lys Ser Ser Met
3020                 3025                3030

Ser Asn Arg Ala Lys Thr Ala Arg Asn Ile Asn Leu Tyr Thr Gly
3035                 3040                3045

Asn Asp Pro Arg Glu Ile Arg Asp Leu Met Ala Glu Gly Arg Ile
3050                 3055                3060

Leu Val Val Ala Leu Arg Asp Ile Asp Pro Asp Leu Ser Glu Leu
3065                 3070                3075

Val Asp Phe Lys Gly Thr Phe Leu Asp Arg Glu Ala Leu Glu Ala
3080                 3085                3090

Leu Ser Leu Gly Gln Pro Lys Pro Lys Gln Val Thr Lys Ala Ala
3095                 3100                3105

Ile Arg Asp Leu Leu Lys Glu Arg Gln Val Glu Ile Pro Asp
3110                 3115                3120

Trp Phe Thr Ser Asp Asp Pro Val Phe Leu Asp Ile Ala Met Lys
3125                 3130                3135

Lys Asp Lys Tyr His Leu Ile Gly Asp Val Val Glu Val Lys Asp
3140                 3145                3150

Gln Ala Lys Ala Leu Gly Ala Thr Asp Gln Thr Arg Ile Val Lys
3155                 3160                3165

Glu Val Gly Ser Arg Thr Tyr Thr Met Lys Leu Ser Ser Trp Phe
3170                 3175                3180

Leu Gln Ala Ser Ser Lys Gln Met Ser Leu Thr Pro Leu Phe Glu
3185                 3190                3195

Glu Leu Leu Leu Arg Cys Pro Pro Ala Thr Lys Ser Asn Lys Gly
3200                 3205                3210

His Met Ala Ser Ala Tyr Gln Leu Ala Gln Gly Asn Trp Glu Pro
3215                 3220                3225

Leu Gly Cys Gly Val His Leu Gly Thr Val Pro Ala Arg Arg Val
3230                 3235                3240
```

```
Lys Met His Pro Tyr Glu Ala Tyr Leu Lys Leu Lys Asp Leu Val
3245                3250                3255

Glu Glu Glu Glu Lys Lys Pro Arg Ile Arg Asp Thr Val Ile Arg
3260                3265                3270

Glu His Asn Lys Trp Ile Leu Lys Lys Ile Lys Phe Gln Gly Asn
3275                3280                3285

Leu Asn Thr Lys Lys Met Leu Asn Pro Gly Lys Leu Ser Glu Gln
3290                3295                3300

Leu Asp Arg Glu Gly His Lys Arg Asn Ile Tyr Asn Asn Gln Ile
3305                3310                3315

Ser Thr Val Met Ser Ser Ala Gly Ile Arg Leu Glu Lys Leu Pro
3320                3325                3330

Ile Val Arg Ala Gln Thr Asp Thr Lys Ser Phe His Glu Ala Ile
3335                3340                3345

Arg Asp Lys Ile Asp Lys Asn Glu Asn Arg Gln Asn Pro Glu Leu
3350                3355                3360

His Asn Lys Leu Leu Glu Ile Phe His Thr Ile Ala Asp Pro Ser
3365                3370                3375

Leu Lys His Thr Tyr Gly Glu Val Thr Trp Glu Gln Leu Glu Ala
3380                3385                3390

Gly Ile Asn Arg Lys Gly Ala Ala Gly Phe Leu Glu Lys Lys Asn
3395                3400                3405

Ile Gly Glu Val Leu Asp Ser Glu Lys His Leu Val Glu Gln Leu
3410                3415                3420

Val Arg Asp Leu Lys Ala Gly Arg Lys Ile Arg Tyr Tyr Glu Thr
3425                3430                3435

Ala Ile Pro Lys Asn Glu Lys Arg Asp Val Ser Asp Asp Trp Gln
3440                3445                3450

Ala Gly Asp Leu Val Asp Glu Lys Lys Pro Arg Val Ile Gln Tyr
3455                3460                3465

Pro Glu Ala Lys Thr Arg Leu Ala Ile Thr Lys Val Met Tyr Asn
3470                3475                3480

Trp Val Lys Gln Gln Pro Val Val Ile Pro Gly Tyr Glu Gly Lys
3485                3490                3495

Thr Pro Leu Phe Asn Ile Phe Asn Lys Val Arg Lys Glu Trp Asp
3500                3505                3510

Leu Phe Asn Glu Pro Val Ala Val Ser Phe Asp Thr Lys Ala Trp
3515                3520                3525

Asp Thr Gln Val Thr Ser Arg Asp Leu His Leu Ile Gly Glu Ile
3530                3535                3540

Gln Lys Tyr Tyr Tyr Arg Lys Glu Trp His Lys Phe Ile Asp Thr
3545                3550                3555

Ile Thr Asp His Met Val Glu Val Pro Val Ile Thr Ala Asp Gly
3560                3565                3570

Glu Val Tyr Ile Arg Asn Gly Gln Arg Gly Ser Gly Gln Pro Asp
3575                3580                3585

Thr Ser Ala Gly Asn Ser Met Leu Asn Val Leu Thr Met Ile Tyr
3590                3595                3600

Ala Phe Cys Glu Ser Thr Gly Val Pro Tyr Lys Ser Phe Asn Arg
3605                3610                3615

Val Ala Lys Ile His Val Cys Gly Asp Asp Gly Phe Leu Ile Thr
3620                3625                3630

Glu Lys Gly Leu Gly Leu Lys Phe Ser Asn Lys Gly Met Gln Ile
```

```
          3635                3640                3645

Leu His Glu Ala Gly Lys Pro Gln Lys Leu Thr Glu Gly Glu Lys
    3650                3655                3660

Met Lys Val Ala Tyr Lys Phe Glu Asp Ile Glu Phe Cys Ser His
    3665                3670                3675

Thr Pro Val Pro Val Arg Trp Ser Asp Asn Thr Ser Ser Tyr Met
    3680                3685                3690

Ala Gly Arg Asp Thr Ala Val Ile Leu Ser Lys Met Ala Thr Arg
    3695                3700                3705

Leu Asp Ser Ser Gly Glu Arg Gly Thr Thr Ala Tyr Glu Lys Ala
    3710                3715                3720

Val Ala Phe Ser Phe Leu Leu Met Tyr Ser Trp Asn Pro Leu Val
    3725                3730                3735

Arg Arg Ile Cys Leu Leu Val Leu Ser Gln Arg Pro Glu Thr Ala
    3740                3745                3750

Pro Ser Thr Gln Thr Thr Tyr Tyr Lys Gly Asp Pro Ile Gly
    3755                3760                3765

Ala Tyr Lys Asp Val Ile Gly Arg Asn Leu Ser Glu Leu Lys Arg
    3770                3775                3780

Thr Gly Phe Glu Lys Leu Ala Asn Leu Asn Leu Ser Leu Ser Thr
    3785                3790                3795

Leu Gly Ile Trp Thr Lys His Thr Ser Lys Arg Ile Ile Gln Asp
    3800                3805                3810

Cys Val Ala Ile Gly Lys Glu Glu Gly Asn Trp Leu Val Asn Ala
    3815                3820                3825

Asp Arg Leu Ile Ser Ser Lys Thr Gly His Leu Tyr Ile Pro Asp
    3830                3835                3840

Lys Gly Phe Thr Leu Gln Gly Lys His Tyr Glu Gln Leu Gln Leu
    3845                3850                3855

Gly Ala Glu Thr Asn Pro Val Met Gly Val Gly Thr Glu Arg Tyr
    3860                3865                3870

Lys Leu Gly Pro Ile Val Asn Leu Leu Leu Arg Arg Leu Lys Val
    3875                3880                3885

Leu Leu Met Ala Ala Val Gly Ala Ser Ser
    3890                3895

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucleotide primer NADL4744

<400> SEQUENCE: 7
cgtggcttct tggtacggg                                               19

<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide primer NADL5305

<400> SEQUENCE: 8
agcggtatat tgtacaaagc ca                                           22

<210> SEQ ID NO 9
```

-continued

```
<211> LENGTH: 24
<212> TYPE: DNA
<213> ORGANISM: Artificial Sequence
<220> FEATURE:
<223> OTHER INFORMATION: synthetic oligonucleotide primer 53637U2

<400> SEQUENCE: 9
tgcacgatct gtgaagggaa agaa                                          24

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide primer NADL4844

<400> SEQUENCE: 10
tgcactgtat gtgagggccg agag                                          24
```